(12) United States Patent
Jackson et al.

(10) Patent No.: US 7,598,377 B2
(45) Date of Patent: *Oct. 6, 2009

(54) INHIBITION OF PHOSPHOINOSITIDE 3-KINASE β

(75) Inventors: Shaun P. Jackson, Victoria (AU); Alan D. Robertson, New South Wales (AU); Vijaya Kenche, Victoria (AU); Philip Thompson, Northcote (AU); Hishani Prabaharan, Victoria (AU); Karen Anderson, Victoria (AU); Belinda Abbott, Burwood (AU); Isaac Goncalves, Victoria (AU); Warwick Nesbitt, Victoria (AU); Simone Shoenwaelder, Victoria (AU); Dilek Saylik, Victoria (AU)

(73) Assignee: AstraZeneca AB, Sodertalje (SE)

(*) Notice: Subject to any disclaimer, the term of this patent is extended or adjusted under 35 U.S.C. 154(b) by 92 days.

This patent is subject to a terminal disclaimer.

(21) Appl. No.: 10/522,777

(22) PCT Filed: Aug. 18, 2003
(Under 37 CFR 1.47)

(86) PCT No.: PCT/IB03/04177

§ 371 (c)(1),
(2), (4) Date: Jul. 6, 2006

(87) PCT Pub. No.: WO2004/016607

PCT Pub. Date: Feb. 26, 2004

(65) Prior Publication Data

US 2006/0276470 A1    Dec. 7, 2006

Related U.S. Application Data

(60) Provisional application No. 60/403,639, filed on Aug. 16, 2002, provisional application No. 60/428,283, filed on Nov. 22, 2002.

(51) Int. Cl.
*C07D 413/04* (2006.01)
(52) U.S. Cl. ...................................... 544/119
(58) Field of Classification Search ................ 544/119, 544/128, 131, 151; 514/233.2, 233.5, 235.5, 514/235.2
See application file for complete search history.

(56) References Cited

U.S. PATENT DOCUMENTS

| | | | |
|---|---|---|---|
| 5,703,075 A | 12/1997 | Gammill et al. | |
| 6,977,255 B2 * | 12/2005 | Robertson et al. | 514/235.2 |
| 7,405,211 B2 * | 7/2008 | Robertson et al. | 514/232.5 |

FOREIGN PATENT DOCUMENTS

WO    WO 0153266    * 7/2001

* cited by examiner

*Primary Examiner*—Bernard Dentz
(74) *Attorney, Agent, or Firm*—Pepper Hamilton LLP

(57) ABSTRACT

The present invention relates to selective inhibitors of phosphoinositide (PI) 3-kinase β, use of the selective inhibitors in anti-thrombotic therapy, and a method for screening compounds useful for the new anti-thrombotic therapy by detecting selective inhibitory activity of PI 3-kinase β of the compound. The invention also relates to novel compounds that are inhibitors of PI 3-kinase.

1 Claim, 7 Drawing Sheets

Neutrophil ROS Response

Neutrophil ROS Response

INHIBITION OF PHOSPHOINOSITIDE 3-KINASE β

BACKGROUND OF THE INVENTION

I. Field of the Invention

The present invention is broadly concerned with a new anti-thrombotic therapy and compounds useful for the new therapy. More particularly, the present invention relates to selective inhibitors of phosphoinositide (PI) 3-kinase β, use of the selective inhibitors in anti-thrombotic therapy and a screening method for a compound useful for the new anti-thrombotic therapy by detecting selective inhibitory activity of PI 3-kinase β of the compound.

II. Description of the Related Art

Platelets are specialized adhesive cells that play a fundamental role in the haemostatic process. Under normal conditions, platelets neither adhere to, nor are activated by the vascular endothelium. However, damage to the endothelium or disruption of plaque exposes the flowing blood to a variety of thrombogenic elements including collagen, fibronectin and von Willebrand factor (vWF). Circulating platelets bear receptors of these thrombogenic elements. Upon vascular injury, platelets, via glycoprotein GP Ib receptor, adhere to specific subendothelial adhesive proteins, such as von Willebrand factor (vWF) at the site of ruptured plaques (platelet adhesion), become activated (platelet activation), and produce a number of substances including adenosine diphosphate (ADP), thrombin, serotonin, and vasoconstrictor thromboxane A2 (TxA2). The activated ADP receptor in turn activates the GP IIb/IIIa receptor on the platelet surface. These receptors become the sites of fibrinogen bridges that link the platelets together (platelet aggregation) and subsequent thrombus formation.

Thus, sudden rupturing or fissuring of advanced atherosclerotic plaques causes an exaggerated platelet adhesion response, which commonly leads to the formation of vaso-occlusive platelet thrombi. The formation of these thrombi in the coronary or cerebral circulation leads to acute myocardial infarction and stroke, respectively, which combined represent the leading causes of death in the industrialized world. Platelet thrombus formation also leads to a number of other clinical states including unstable angina, sudden death, transient ischemic attacks, amaurosis fugax, and acute ischemia of limbs and internal organs. A number of factors that contribute to increase of thrombogenic potential of ruptured plaques include (1) the high reactivity of adhesive substrates in the plaque, (2) the presence of tissue factor in the lesion, and (3) the indirect platelet activating effects of high shear caused by narrowing of the vessel lumen by the atherothrombotic process.

The existing anti-thrombotic therapies mainly target one or more key steps in the thrombotic process. That is, anti-coagulants and anti-platelet agents are frequently used to alleviate thrombosis. Blood clotting can be minimized or eliminated in many instances by administering a suitable anti-coagulant, including one or more of a coumarin derivative (e.g., warfarin and dicumarol) or a charged polymer (e.g., heparin, hirudin or hirulog), or through the use of an anti-platelet agent (e.g, aspirin, clopidogrel, ticlopidine, dipyridimole, or one of several GPIIb/IIIa receptor antagonists). Anti-coagulants and platelet inhibitors suffer from a significant limitation, however, due to side effects such as hemorrhaging, re-occlusion, "white-clot" syndrome, irritation, birth defects, thrombocytopenia, and hepatic dysfunction. Moreover, long-term administration of anti-coagulants and platelet inhibitors can particularly increase risk of life-threatening illness or hemorrhage.

Thus, to avoid the aforementioned drawbacks of the existing anti-thrombotic therapy, there exists a need to develop a new anti-thrombotic therapy selectively targeting a process that is critical to pathological thrombus formation without interfering with normal haemostasis.

Rheological disturbances (high shear and turbulent flow) play a major role in promoting pathological thrombosis, and thus one such strategy would be to attenuate the platelet activating effects of high shear stress by targeting mechano-sensory elements in platelets. However, before the instant invention, signaling events that are important for shear-induced platelet activation, but not for haemostasis, have not been identified.

SUMMARY OF THE INVENTION

Thus, it is an object of the present invention to provide a method of disrupting platelet aggregation and adhesion occurring under high shear conditions comprising administering an effective amount of a selective PI 3-kinase inhibitor to a patient in need thereof.

It is a further object of the present invention to provide an antithrombotic method comprising administering an effective amount of a selective PI 3-kinase β inhibitor to a patient in need thereof. According to the method, specific inhibition of thrombosis can be obtained without affecting normal haemostasis by targeting PI 3-kinase β that is important for shear-induced platelet activation. The present invention therefore does not involve side effects caused by disruption of normal haemostasis, such as extending of bleeding time.

Accordingly, it is another object of the present invention to provide a method for inhibiting platelet activation induced by shear, comprising administering an effective amount of a selective PI 3-kinase β inhibitor to a patient in need thereof. It is also an object of the present invention to provide a method for preventing or treating cardiovascular disease, such as coronary artery occlusion, stroke, acute coronary syndrome, acute myocardial infarction, restenosis, atherosclerosis, and unstable angina, by administering an effective amount of a selective PI 3-kinase β inhibitor to a patient in need thereof. In this method, the use of the selective PI 3-kinase β inhibitor enables to avoid side effects caused by disruption of normal haemostasis, such as extending of bleeding time.

It is preferred that the methodology of the present invention uses a selective PI 3-kinase β inhibitor that is identified by an approach that comprises contacting a candidate compound with isolated PI 3-kinase isoforms, detecting inhibitory effects of said compound to each isoform, wherein comparison of detected effect of said compound on each isoform determines said compound as the selective PI 3-kinase β inhibitor.

It is another object of the present invention, therefore, to provide a screening method for a selective PI 3-kinase β, comprising contacting a candidate compound with isolated PI 3-kinase isoforms, detecting inhibitory effects of said compound to each isoform, wherein comparison of detected effect of said compound on each isoform determines said compound as the selective PI 3-kinase β inhibitor.

It is preferred that the selective PI 3-kinase β inhibitor is at least about $\geq$10-fold, more preferably $\geq$20-fold, more preferably $\geq$30-fold, selective for inhibition of PI 3-kinase β relative to other Type I PI 3-kinase isoforms in a biochemical assay. Such other Type I PI3-kinases include PI 3-kinase α,γ and δ.

Another object of the invention relates to a method for antithrombosis comprising administering an effective amount of a selective PI 3-kinase β inhibitor to a patient in need thereof, provided that the inhibitor is not according to formula (II):

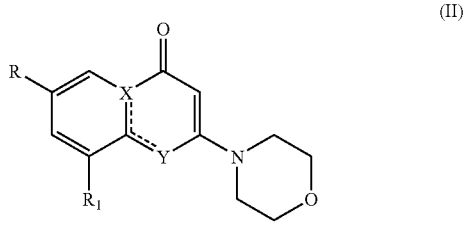

(II)

wherein,

R is H, OH, F, Cl, Br, I, $C_1$-$C_6$ alkyl, aryl or $(CH_2)_n$-aryl;

$R^1$ is H, OH, F, Cl, Br, I, $C_1$-$C_6$ alkyl, $C_3$-$C_6$ cycloalkyl, CH=CH-aryl, C≡C-aryl, $(CHR^3)_n$-aryl, $NR^3$—$C_1$-$C_6$ alkyl, $NR^3$-cycloalkyl, $NR^3$—$(CHR^3)_n$-aryl, $(CHR^3)_n$—$NR^3$-alkyl, $(CHR^3)_n$—$NR^3$-cycloalkyl, $(CHR^3)_n$—O-aryl, $(CHR^3)_n$—O-alkyl, $(CHR^3)_n$—O-cycloalkyl, O—$(CHR^3)_n$-aryl, S—$(CHR^3)_n$-aryl, or CO-aryl, wherein n is 0, 1, or 2 and alkyl, cycloalkyl or aryl is optionally substituted with F, Cl, Br, I, CN, $CO_2H$, $CO_2R^3$, $NO_2$, $CF_3$, substituted or unsubstituted $C_1$-$C_6$ alkyl, substituted or unsubstituted cycloalkyl, substituted or unsubstituted aryl, $OCF_3$, $OR^3$, $OSO_2$-aryl, substituted or unsubstituted amine, $NHCOR^3$, $NHSO_2R^3$, $CONHR^3$, or $SO_2NHR^3$; and $R^3$ is H, or substituted or unsubstituted $C_1$-$C_6$ alkyl, substituted or unsubstituted aryl;

except where the compound of formula (II) is selected from the group consisting of:

9-(3-pyridinylmethyl)oxy-2-morpholinyl-4H-pyrido[1,2-a]pyrimidin-4-one (TGX-140);

7-methyl-9-phenylaminomethyl-2-morpholinyl-4H-pyrido[1,2-a]pyrimidin-4-one (TGX-183);

8-(4-methylphenl)2-)4-morpholinyl)-4(1H)-quinolinone (TGX-113);

8-(4-fluorophenoxy)-2-(4-morpholinyl)-4(1H)-quinolinone (TGX-121);

2-morpholinyl-8-(phenylmethyl)-4H-1-benzopyran-4-one (TGX-90);

2-(4-morpholinyl)-8-(4-fluoro-2-methylphenyl)oxy-4H-1-benzopyran-4-one (TGX-184);

9-[[(2-chlorophenyl)-methyl]amino-7-methyl-2-(4-morpholinyl)-4H-pyrido[1,2-a]pyrimidin-4-one (TGX-167);

9-[[(2-methoxyphenyl)-methyl]amino]-7-methyl-2-(4-morpholinyl)-4H-pyrido[1,2-a]pyrimidin-4-one (TGX-137);

7-methyl-2-(4-morpholinyl)-9-[(phenylmethyl)amino]-4H-pyrido[1,2-a]pyrimidin-4-one (TGX-126);

9-[[(4-fluoro-2-methylphenyl)amino]-7-methyl-2-(4-morpholinyl)-4H-pyrido[1,2-a]pyrimidin-4-one (TGX-170);

7-methyl-2-(4-morpholinyl)-9-[[(1R)-1-phenylethyl]amino]-4H-pyrido[1,2-a]pyrimidin-4-one (TGX-123);

7-methyl-2-(4-morpholinyl)-9-[(2-pyridinylmethyl)amino]-4H-pyrido[1,2-a]pyrimidin-4-one (TGX-161);

9-[[(4-chlorophenyl)methyl]amino]-7-methyl-2-(4-morpholinyl)-4H-pyrido[1,2-a]pyrimidin4-one (TGX-108);

2-(4-morpholinyl)-9-(phenylmethyl)-4H-pyrido[1,2-a]pyrimidin-4-one (TGX-040);

7-methyl-9-(N-Methyl-N-phenyl)aminomethyl-2-(4-morpholinyl)-4H-pyrido[1,2-a]pyrimidin-4-one (TGX-195);

2-(4-morpholinyl)-8-(phenylmethyl)oxy-4H-1-benzopyran-4-one (TGX-102);

2-(4-morpholinyl)-8-(phenylmethyl)amino-4H-1-benzopyran-4-one (TGX-204);

2-(4-morpholinyl)-8-phenylamino-4H-benzopyran-4-one (TGX-324);

8-(3-chlorophenyl)oxy-2-(4-morpholinyl)-4H-1-benzopyran-4-one (TGX-259);

8-(3-methylphenyl)-2-(4-morpholinyl)-4(1H)-quinolinone (TGX-127);

8-(2-fluorophenyl)-2-(4-morpholinyl)-4(1H)-quinolinone (TGX-143);

(±)-7-methyl-2-morpholin-4-yl-9-[1-(3-pyridinylamino)ethyl]-pyrido[1,2-a]pyrimidin-4-one (KN-304).

In another object of the invention, the method of antithrombosis involves administration of a selective PI 3-kinase β inhibitor according to formula (I):

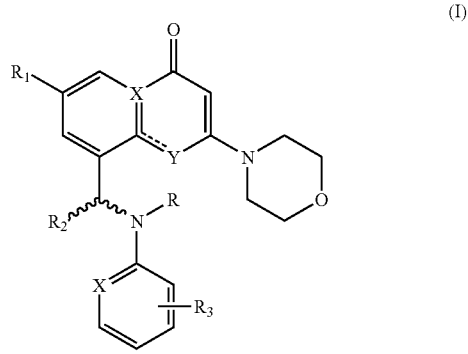

(I)

wherein,

R is H, $C_1$-$C_6$ branched or straight chain alkyl, or aryl or $(CH_2)_n$-aryl;

$R_1$ is H, OH, $OCH_3$, $OCF_3$, F, Cl, $CF_3$, $C_1$-$C_6$ branched or straight chain alkyl, or aryl or $(CH_2)_n$-aryl;

$R_2$ is H, $C_1$-$C_6$ branched or straight chain alkyl, or aryl or $(CH_2)_n$-aryl in either the R or the S configuration $R_3$ is one or more of H, F, Cl, Br, I, CN, $CO_2H$, $CO_2R$, $NO_2$, $CF_3$, substituted or unsubstituted $C_1$-$C_6$ alkyl, substituted or unsubstituted cycloalkyl, substituted or unsubstituted aryl $OCH_3$, $OCH_2F$, $OCHF_2$, $OCF_3$, OR, $OSO_2$-aryl, substituted or unsubstituted amine, NHCOR, $NHSO_2R$, CONHR, or $SO_2NHR$ X is C or N and Y is N or O.

In yet another object of the invention, the method of antithrombosis involves administration of a selective PI 3-kinase β inhibitor according to formula (III):

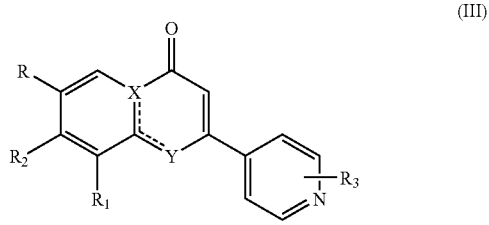

(III)

where X and Y are C and O respectively, or C and NH respectively, or both N.

R is H, OH, OCH$_3$, OCF$_3$, F, Cl, Br, I, C$_1$-C$_6$ alkyl, aryl or (CH$_2$)$_n$-aryl;

R$_1$, R$_2$ and R$_3$ are independently H, OH, F, Cl, Br, I, C$_1$-C$_6$ alkyl, C$_3$-C$_6$ cycloalkyl, CH=CH-aryl, C≡C-aryl, (CHR$^{13}$)$_n$-aryl, NR$^{13}$—C$_1$-C$_6$ alkyl, NR$^{13}$-cycloalkyl, NR$^{13}$—(CHR$^{13}$)$_n$-aryl, (CHR$^{13}$)$_n$—NR$^{13}$-aryl, (CHR$^{13}$)$_n$—NR$^{13}$-alkyl, (CHR$^{13}$)$_n$—NR$^{13}$-cycloalkyl, (CHR$^{13}$)$_n$—O-aryl, (CHR$^{13}$)$_n$—O-alkyl, (CHR$^{13}$)$_n$—O-cycloalkyl, O—(CHR$^{13}$)$_n$-aryl, S—(CHR$^{13}$)$_n$-aryl, or CO-aryl, wherein n is 0,1, or 2 and alkyl, cycloalkyl or aryl is optionally substituted with F, Cl, Br, I, CN, CO$_2$H, CO$_2$R$^{13}$, NO$_2$, CF$_3$, substituted or unsubstituted C$_1$-C$_6$ alkyl, substituted or unsubstituted cycloalkyl, substituted or unsubstituted aryl, OCF$_3$, OR$^{13}$, OSO$_2$-aryl, substituted or unsubstituted amine, NHCOR$^{13}$, NHSO$_2$R$^{13}$, CONHR$^{13}$, or SO$_2$NHR$^{13}$; and R$^{13}$ is H, or substituted or unsubstituted C$_1$-C$_6$ alkyl, substituted or unsubstituted aryl.

An object of the invention relates to novel compounds having the following formula (III):

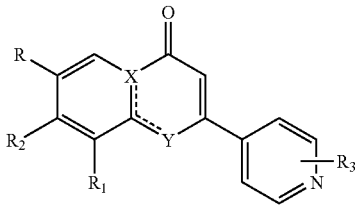

(III)

where X and Y are C and O respectively, or C and NH respectively, or both N.

R is H, OH, OCH$_3$, OCF$_3$, F, Cl, Br, I, C$_1$-C$_6$ alkyl, aryl or (CH$_2$)$_n$-aryl;

R$_1$R$_2$ and R$_3$ are independently H, OH, F, Cl, Br, I, C$_1$-C$_6$ alkyl, C$_3$-C$_6$ cycloalkyl, CH=CH-aryl, C≡C-aryl, (CHR$^{13}$)$_n$-aryl, NR$^{13}$—C$_1$-C$_6$ allyl, NR$^{13}$-cycloalkyl, NR$^{13}$-(CHR$^{13}$)$_n$-aryl, (CHR$^{13}$)$_n$-NR$^{13}$-aryl, (CHR$^{13}$)$_n$—NR$^{13}$-alkyl, (CHR$^{13}$)$_n$—NR$^{13}$-cycloalkyl, (CHR$^{13}$)$_n$—O-aryl, (CHR$^{13}$)$_n$—O-alkyl, (CHR$^{13}$)$_n$—O-cycloalkyl, O—(CHR$^{13}$)$_n$-aryl, S—(CHR$^{13}$)$_n$-aryl, or CO-aryl, wherein n is 0,1, or 2 alkyl, cycloalkyl or aryl is optionally substituted with F, Cl, Br, I, CN, CO$_2$H, CO$_2$R$^{13}$, NO$_2$, CF$_3$, substituted or unsubstituted C$_1$-C$_6$ alkyl, substituted or unsubstituted cycloalkyl, substituted or unsubstituted aryl, OCF$_3$, OR$^{13}$, OSO$_2$-aryl, substituted or unsubstituted amine, NHCOR$^{13}$, NHSO$_2$R$^{13}$, CONHR$^{13}$, or SO$_2$NHR$^{13}$; and R$^{13}$ is H, or substituted or unsubstituted C$_1$-C$_6$ alkyl, substituted or unsubstituted aryl.

In another object of the invention, the method of antithrombosis involves administration of a 2-morpholino-substituted derivative of formula (I) wherein:

R is H, C$_1$-C$_6$ branched or straight chain alkyl or aryl;

R$_1$ is H, OH, OCH$_3$, OCF$_3$, F, Cl, CF$_3$, C$_1$-C$_6$ branched or straight chain alkyl;

R$_2$ is H, C$_1$-C$_6$ branched or straight chain alkyl, or aryl in either the R or the S configuration R$_3$ is one or more of H, F, Cl, Br, CN, CO$_2$H, CO$_2$R, NO$_2$, CF$_3$, branched or straight chain C$_1$-C$_6$ alkyl, substituted or unsubstituted cycloalkyl, substituted or unsubstituted aryl, OCH$_3$, OCH$_2$F, OCHF$_2$, OCF$_3$, OR, substituted or unsubstituted amine, NHCOR, NHSO$_2$R, CONHR, or SO$_2$NHR X is C or N and Y is N or O.

In another object of the invention, the method of antithrombosis involves administration of a PI 3-kinase inhibitor which is selected from the group consisting of:

(±)-7-methyl-9-{[methyl(phenyl)amino]methyl}-2-morpholin-4-yl-pyrido[1,2-a]pyrimidin4-one (TGX-195);

(±)-7-methyl-2-morpholin-4-yl-9-(1-phenylaminoethyl)-pyrido[1,2-a]pyrimidin-4-one (TGX-221);

(±)-7-methyl-2-morpholin-4-yl-9-[1-(4-fluorophenylamino)ethyl]-pyrido[1,2-a]pyrimidin-4-one (TGX-224);

(±)-9-[1-(3,4-difluorophenylamino)ethyl]-7-methyl-2-morpholin-4-yl-pyrido[1,2-a]pyrimidin4-one (TGX-237);

(±)-9-[1-(2,5-difluorophenylamino)ethyl]-7-methyl-2-morpholin-4-yl-pyrido[1,2-a]pyrimidin-4-one (TGX-238);

(±)-9-[1-(3,5-difluorophenylamino)ethyl]-7-methyl-2-morpholin-4-yl-pyrido[1,2-a]pyrimidin-4-one (TGX-239);

(±)-9-[1-(4-fluoro-2-methylphenylamino)ethyl]-7-methyl-2-morpholin-4-yl-pyrido[1,2-a]pyrimidin-4-one (TGX-240);

(±)-9-[1-(4-chlorophenylamino)ethyl]-7-methyl-2-morpholin-4-yl-pyrido[1,2-a]pyrimidin-4-one (TGX-243);

(±)-9-[1-(3,4-dichlorophenylamino)ethyl]-7-methyl-2-morpholin-4-yl-pyrido[1,2-a]pyrimidin4-one (TGX-244);

(±)-9-[1-(3fluorophenylamino)ethyl]-7-methyl-2-morpholin-4-yl-pyrido[1,2-a]pyrimidin-4-one (TGX-247);

(±)-9-[1-(3-chlorophenylamino)ethyl]-7-methyl-2-morpholin-4-yl-pyrido[1,2-a]pyrimidin-4-one (TGX-248);

(±)-7-methyl-2-morpholin-4-yl-9-[1-(2-thiazolylamino)ethyl]-pyrido[1,2-a]pyrimidin-4-one (TGX-261);

(±)-7-methyl-9-[1-(3-methylphenylamino)ethyl]-2-morpholin-4-yl-pyrido[1,2-a]pyrimidin-4-one (TGX-262);

(±)-7-methyl-2-morpholin-4-yl-9-[1-(3-trifluoromethylphenylamino)ethyl]-pyrido[1,2-a]pyrimidin-4-one (TGX-264); and (±)-7-methyl-2-morpholin-4-yl-9-[1-(2-pyridinylamino)ethyl]-pyrido[1,2-a]pyrimidin-4-one (TGX-295).

(±)-2-({1-[7-methyl-2-(morpholin4-yl)-4-oxo-pyrido[1,2-a]pyrimidin-9-yl]ethyl}amino)benzoic acid (KN-309);

(±) methyl 2-({1-[7-methyl-2-(morpholin-4-yl)-4-oxo-pyrido[1,2-a]pyrimidin-9-yl]ethyl}amino)benzoate (KN-321);

(±)-2-({1-[7-methyl-2-(morpholi-4-yl)-4-oxo-pyrido[1,2-a]pyrimidin-9-yl]ethyl}amino)benzonitrile (KN-320);

(±)-7-methyl-2-(morpholin-4-yl)-9-(1-{[2-(2H-tetrazol-5-yl)phenyl]amino}ethyl)-pyrido[1,2-a]pyrimid-4-one (KN-325);

(±)-2-(4-morpholinyl)-8[1-(phenylamino)ethyl]-4H-1-benzopyran-4-one (TGX-280).

It is an object of the invention to provide compound according to Formula (III), where R$^1$ is selected from a group consisting of, CH$_3$, C$_2$H$_5$,

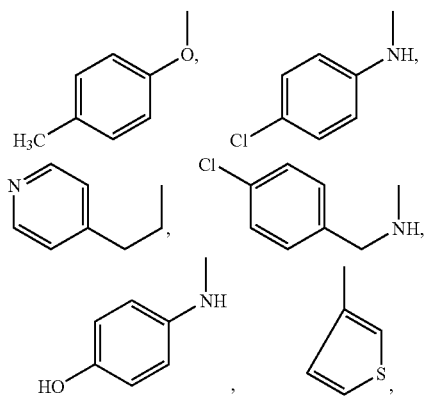

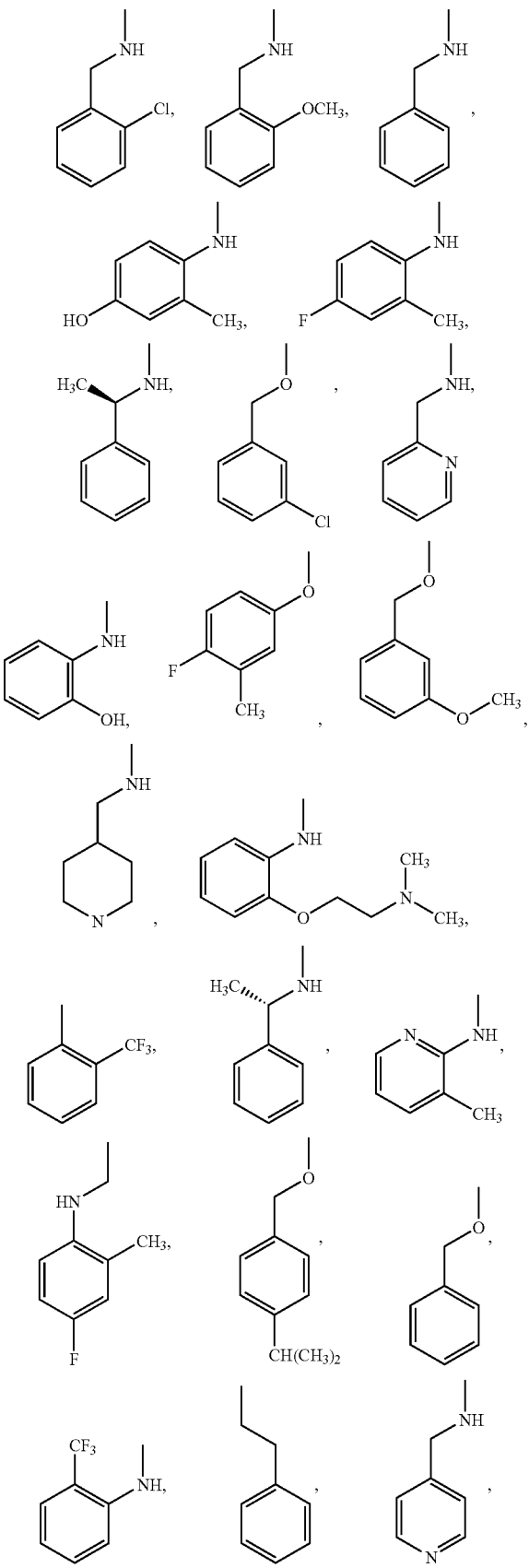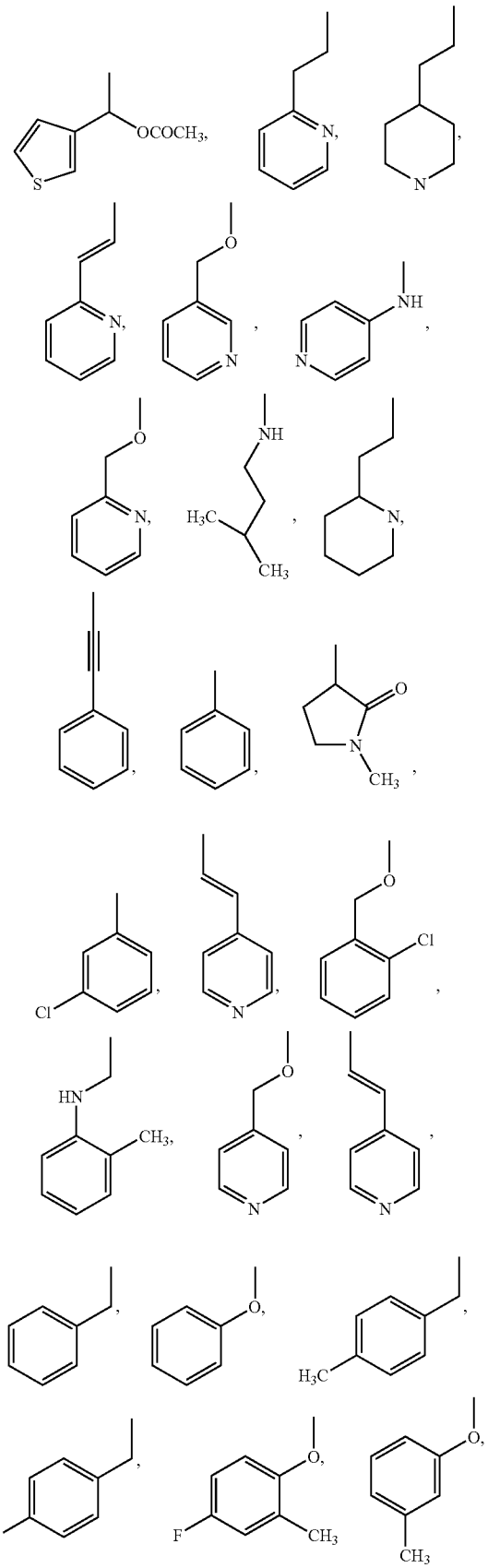

-continued

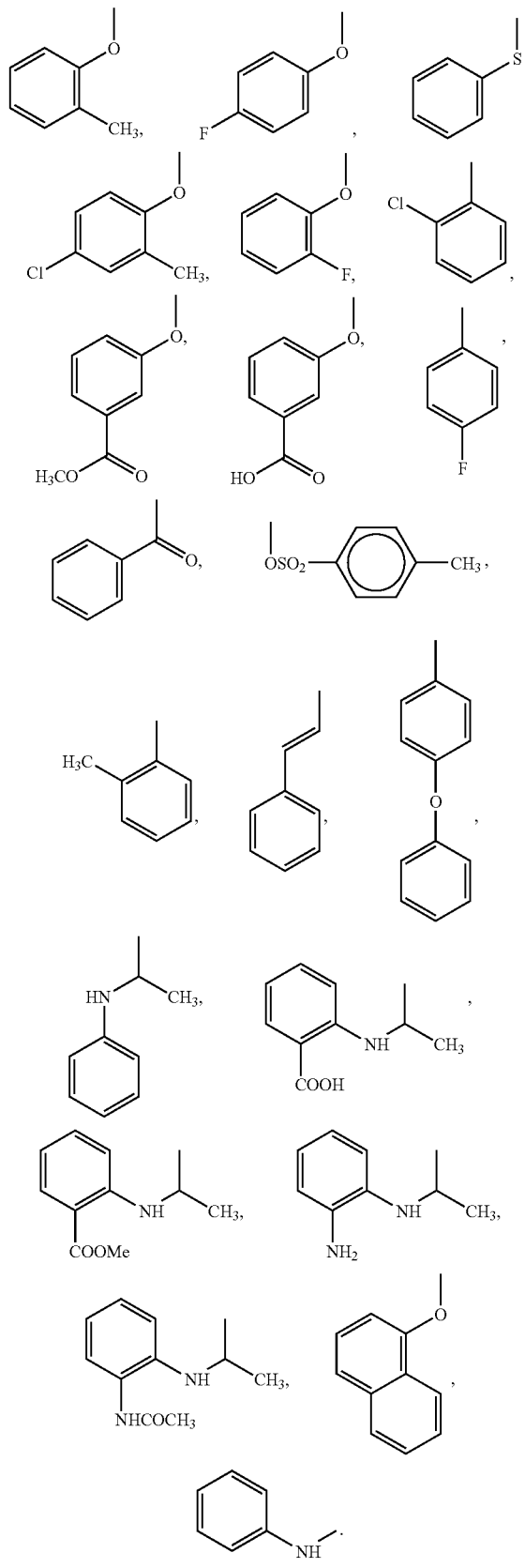

A specific compound according to formula (III), wherein R is methyl and $R^1$ is

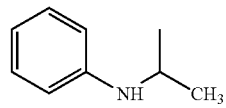

is also contemplated.

A specific compound according to formula (III), wherein R is methyl and $R^1$ is

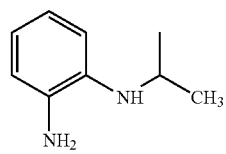

is also contemplated.

A specific compound according to formula (III), wherein R is methyl and $R^1$ is

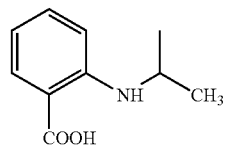

is also contemplated.

A specific compound according to formula (III), wherein R is H and $R^1$ is

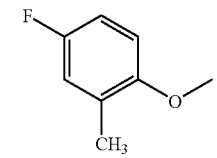

is also contemplated.

A specific compound according to formula (III), wherein R is H and $R^1$ is

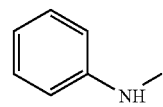

is also contemplated.

The present invention also contemplates a method for inhibiting phosphoinositide 3-kinase in a patient, comprising administering to a patient an amount of the compound of Formula (III) effective in inhibiting the phosphoinositide 3-kinase in the patient.

The present invention also contemplates a method for preventing or treating cardiovascular disease comprising administering an effective amount of the compound of Formula (III) to a patient in need thereof.

The present invention also contemplates a method for preventing or treating respiratory disease comprising administering an effective amount of the compound of Formula (III) to a patient in need thereof.

The present invention also contemplates a method for preventing or treating cancer comprising administering an effective amount of the compound of Formula (III) to a patient in need thereof.

The present invention also contemplates a method for preventing or treating disease linked to disordered white blood cell function comprising administering an effective amount of the compound of Formula (III) to a patient in need thereof.

One object of the inventive method involves administration of the inhibitor below:

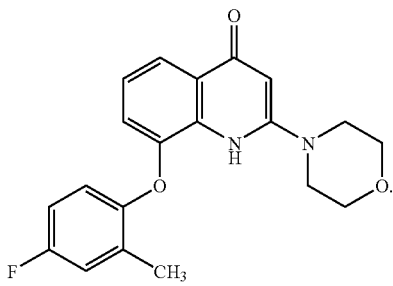

One object of the inventive method involves administration of 6-methyl-8-[1-(phenylamino)ethyl]-2-(4-pyridinyl)-4H-benzopyran-4-one.

One object of the inventive method involves administration of 6-methyl-8-{1-[(2-aminophenyl)amino]ethyl}-2-(4-pyridinyl)-4H-benzopyran-4-one.

The invention also relates to novel compounds selected from the group consisting of: (±)-7-methyl-2-morpholin-4-yl-9-(1-phenylaminoethyl)-pyrido[1,2-a]pyrimidin-4-one;

(±)-2-({1-[7-methyl-2-(morpholin4-yl)4-oxo-pyrido[1,2-a]pyrimidin-9-yl]ethyl}amino)benzoic acid;

(±)-2-({1-[7-methyl-2-(morpholin-4-yl)-4-oxo-pyrido[1,2-a]pyrimidin-9-yl]ethyl}amino)benzonitrile;

(±) methyl 2-({1-[7-methyl-2-(morpholin-4-yl)-4-oxo-pyrido[1,2-a]pyrimidin-9-yl]ethyl}amino)benzoate and (±)-7-methyl-2-(morpholin-4-yl)-9-(1-{[2-(2H-tetrazol-yl)phenyl]amino}ethyl)-pyrido[1,2-a]pyrimid-4-one.

Thus, it is yet another object of the present invention to provide a method of inhibiting PI 3-kinase β comprising administering to the patient an amount of one of the compounds having formula I, wherein the amount is effective in inhibiting the PI 3-kinase β in the patient.

BRIEF DESCRIPTION OF THE DRAWINGS

FIG. 1A shows graphically the proportion of platelets interacting with vWf that form irreversible adhesions under various blood flow conditions. In graph (i), isolated platelets were perfused over the vWf matrix at constant shear rates (600, 1800 or 10,000.s$^{-1}$) and in graph (ii) isolated platelets were allowed to settle on the vWf matrix and subsequently accelerated through a shear rate gradient ($\uparrow\Delta\gamma$) of 10,000.s$^{-2}$.

FIG. 1B demonstrates the behavior of individual platelets at the surface of immobilized vWf; the graphs represent cytosolic calcium flux ($\Delta[Ca^{2+}]_c$) profiles and concomitant displacement (μm) of individual platelets versus time (sec). Isolated platelets were allowed to settle onto the vWf surface prior to the application of accelerating shear rate ($\uparrow\Delta\gamma$) over a 1-sec interval. The arrow (↓) indicates the point of shear application: Sustained, platelet undergoing oscillatory $\Delta[Ca^{2+}]_c$ in association with stationary adhesion; Transient, platelet undergoing a $\Delta[Ca^{2+}]_c$ spike with concomitant transient stationary adhesion; Rolling, platelet displaying minimal $\Delta[Ca^{2+}]_c$ and rapid translocation on the vWf surface.

FIG. 1C shows graphically the proportion of vWf adherent platelets displaying sustained, transient or rolling behaviours, following pre-treatment with vehicle (DMSO<0.25% v/v), 0.5 U/ml apyrase, 1 mM aspirin or 25 μM LY294002.

FIG. 1D shows representative single platelet recordings demonstrating GPIb/V/IX dependent $\Delta[Ca^{2+}]_c$ at the surface of immobilized vWf following treatment with the modulator of GP1b/V/IX binding, Ristocetin (1 mg/ml). Platelets were treated with the integrin $\alpha_{IIb}\beta_3$ antagonists, Aggrastat (200 nM) for 10-min prior to assay: Static, platelets were allowed to settle on the surface of vWf coated cover slips in the absence of shear for 10-min at 37° C. $\Delta[Ca^{2+}]_c$ was monitored for 1.5 minutes at 10 minutes; Constant γ, platelets were perfused over a vWf matrix at a constant shear rate of 1800.s$^{-1}$; $\uparrow\Delta\gamma$ (0-10,000.s$^{-1}$), platelets were allowed to settle on the surface of immobilized vWf followed by a progressive increase in γ to 10,000.s$^{-1}$ over a 1-sec interval. The arrow (↓) shows the point of shear application; +LY294002, $\uparrow\Delta\gamma$ was applied to platelets pre-treated for 10-min with 20 μM of the PI 3-kinase inhibitor LY294002.

FIG. 1E shows the proportion of GPIb/V/IX adherent platelets displaying high frequency $\Delta[Ca^{2+}]_c$ in response to $\uparrow\Delta\gamma$ over 1-sec or 60-sec time interval.

Characterization of a Novel PI 3-kinase β Isoform Selective Inhibitor

Figure 2:
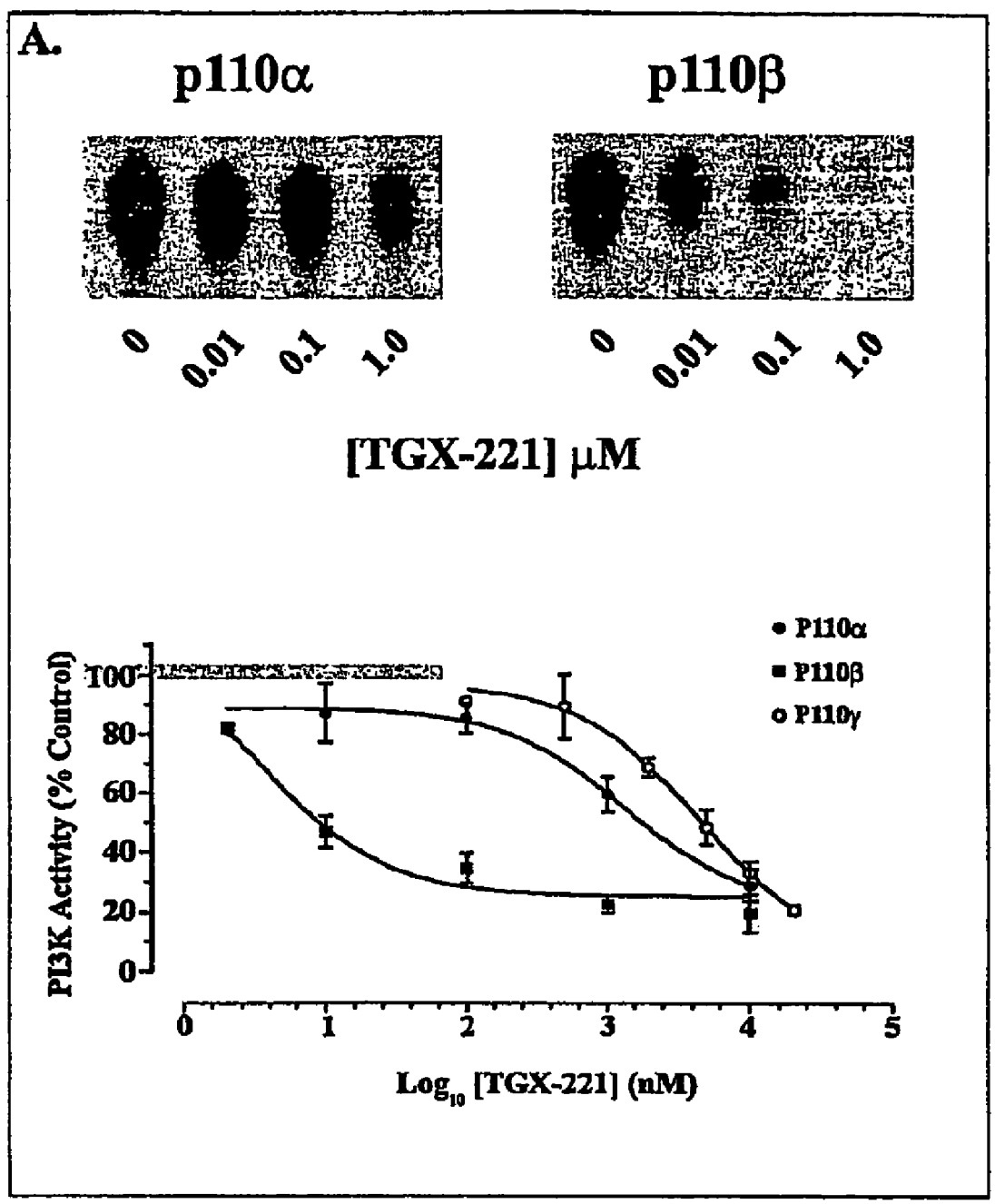

FIG. 2A displays the selectivity of TGX 221, performed using isolated PI 3-kinase isoforms, where activity is measured by the generation of the PI 3-kinase product Phosphatidylinositol 3-Phosphate (PtdIns(3)P). The top panel illustrates the detection of PtdIns(3)P generation using thin layer chromatography and the dose response inhibition by TGX-221 in p110α and p110β isoforms. The line graph represents a dose-response curve of TGX-221 inhibition of the three major platelets PI 3 kinase isoforms, p110α, p110β and p110γ.

Functional Analysis of TGX-221

Figure 3:
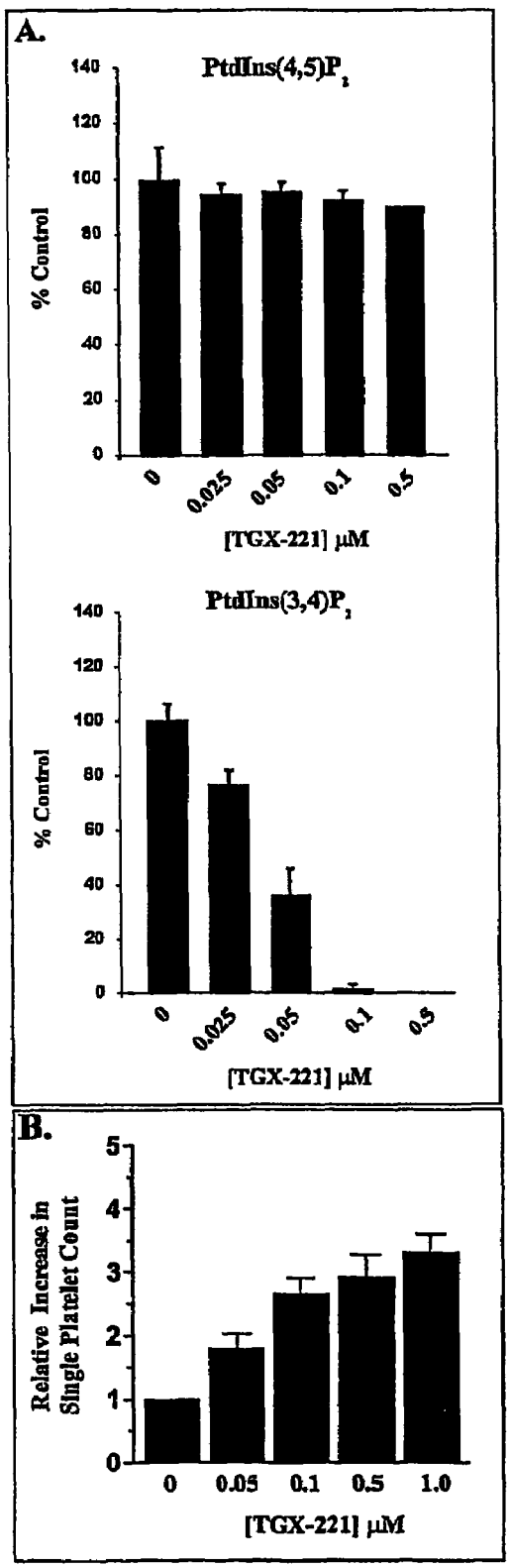

FIG. 3A shows bar graphs representing dose-response inhibition by TGX-221 on lipid generation in platelets following activation by shear (5000 sec$^{-1}$, 2 min) in a cone-and-plate viscometer. Following application to the cone and plate device, platelet samples were subsequently aspirated and single platelet counts analyzed using a Sysmex KN-21N haematology analyzer.

FIG. 3B shows a bar graph illustrating the proportional increase in single platelet counts relative to untreated (control) samples, in various concentrations of TGX-221.

Measurements of the lipid products PtdIns(4,5)P$_2$ and PtdIns(3,4)P$_2$ in intact platelets were performed by initially isolating lipids by HPLC and identifying lipid peaks using defined PtdIns(4,5)P$_2$ and PtdIns(3,4)P$_2$ standards. Lipids were integrated and normalized to total lipid applied and expressed as a fraction of untreated (control) samples.

Demonstration that Inhibition of PI 3-kinase by TGX-221 Eliminates Platelet Responses to Accelerated Shear:—

Figure 4:
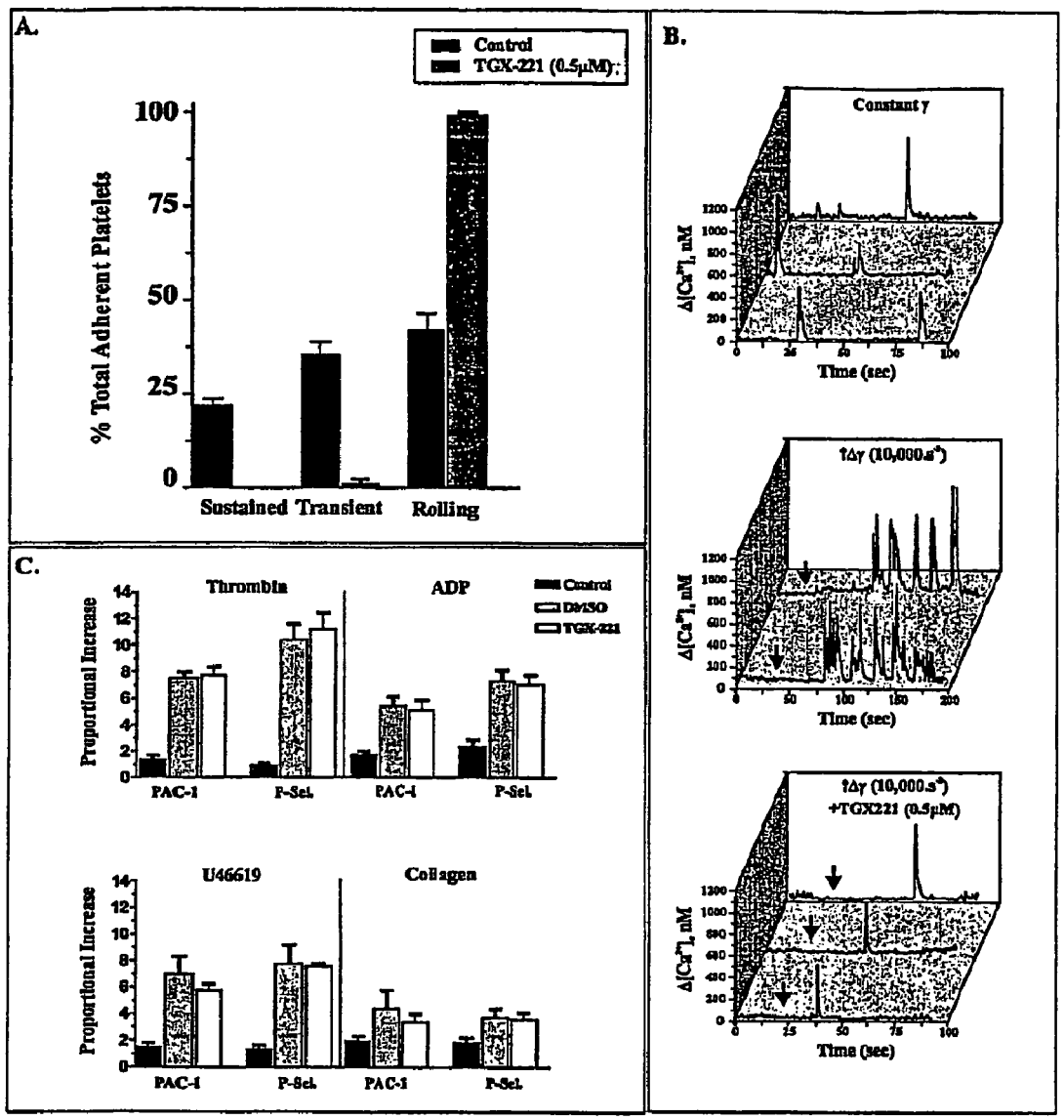

FIG. 4A shows a bar graph of population analysis demonstrating the effect of pre-treatment with 0.5 µM TGX-221 on the proportion of vWf adherent platelets displaying sustained, transient or rolling behaviours (described above) following exposure to a shear rate gradient ($\uparrow\Delta\gamma$) up to $10,000.s^{-1}$ over a 1-sec interval.

FIG. 4B shows representative single platelet recordings demonstrating GPIb/V/IX dependent $\Delta[Ca^{2+}]_c$ at the surface of vWf. As described above, Constant $\gamma$; platelets exposed to constant shear rate of 1800 $s^{-1}$, $\uparrow\Delta\gamma$ ($10,000.s^{-2}$); platelets exposed to shear accelerations, $\uparrow\Delta\gamma$ ($10,000.s^{-2}$)+TGX-221 (0.5 µM); $\uparrow\Delta\gamma$ was applied to platelets pre-treated for 10-min with 0.5 µM TGX-221.

FIG. 4C shows FACS analysis illustrating the level of integrin $\alpha_{IIb}\beta_3$ activation (determined by PAC-1 binding) and surface expression of P-Selectin following physiological agonist stimulation; Control, platelets resuspended in Tyrodes buffer+1 mM $CaCl_2/MgCl_2$ (no agonist treatment); DMSO, platelets pre-treated with 0.25% DMSO (vehicle) prior to agonist stimulation; TGX-221, platelets pre-treated with 0.5 mM TGX-221 10 min prior to agonist stimulation. Agonists: Thrombin, 1 U/ml; ADP, 12.5 mM; U46619, 1 µM; Soluble collagen 10 µg/ml.

In Vivo Antithrombotic Activity of TGX-221

Figure 5:
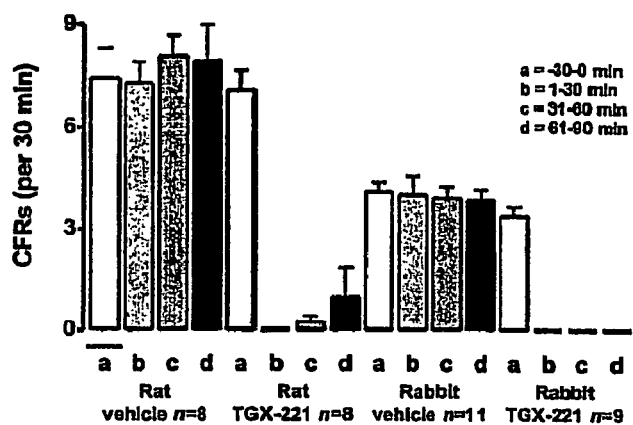
Figure 5:
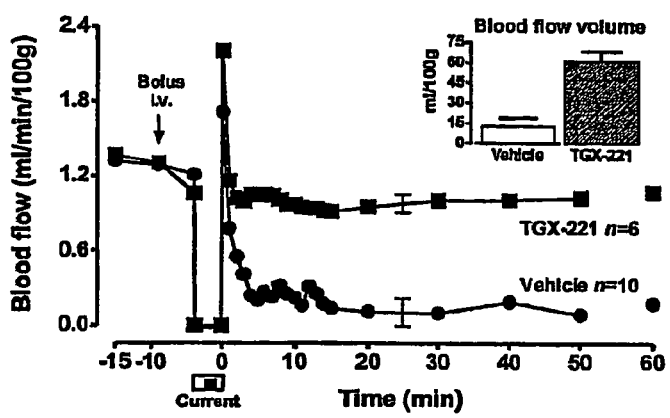
Figure 5:
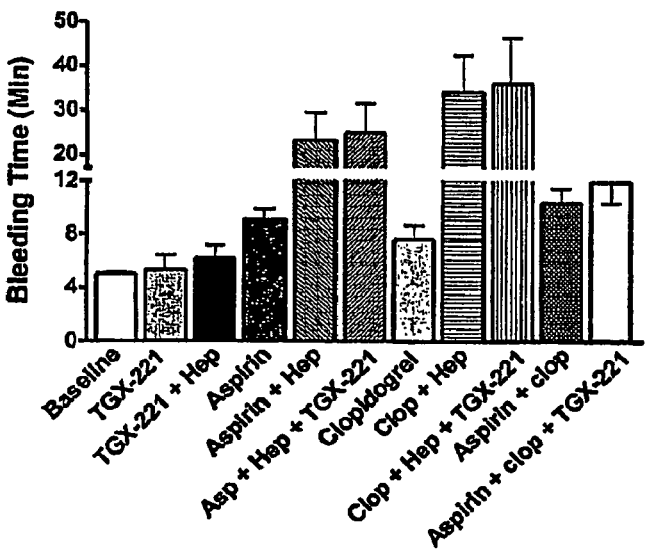

FIG. 5A shows, in a Folts model, effects of vehicle (propylene glycol) or TGX-221 on average number of cyclic carotid artery blood flow reductions (CFRs) per 30 min period pre-drug (a; −30-0 min) and post-drug administration (b-d; 1-30, 31-60 & 61-90 min, respectively) in pentobarbitone-anaesthetised rats (A) and rabbits (B). CFRs were monitored for 30 min before and 90 min after drug administration. n: number of animals. Error bars are ±1 SEM.

FIG. 5B shows, in an Electrolytic model, effects of vehicle (propylene glycol) or TGX-221 on carotid artery blood flow (ml/min per 100 g body weight) after electrolytic injury (7 mA current for 4 min (time—4-0 min) with zero blood flow; artery clamp released at 0 min) in pentobarbitone-anaesthetised rats. Treatments were given as an i.v. bolus at time−9 min (i.e. 5 min before applying the current). Error bars are average SEM from repeated-measures ANOVA. FIG. 5B insert demonstrates the: effect of treatments on carotid artery blood flow volume (area under the blood flow curve over the 60 min post-stimulation period) after electrolytic injury in anaesthetized rats. Error bars are ±1 SEM.

FIG. 5C shows comparison of rat tail bleeding time in halothane-anaesthetized rats treated with TGX-221, TGX-221+heparin, aspirin, clopidogrel, clopidogrel+heparin, clopidogrel+heparin+TGX-221, aspirin+heparin, and aspirin+heparin+TGX-221, respectively.

Figure 6A:
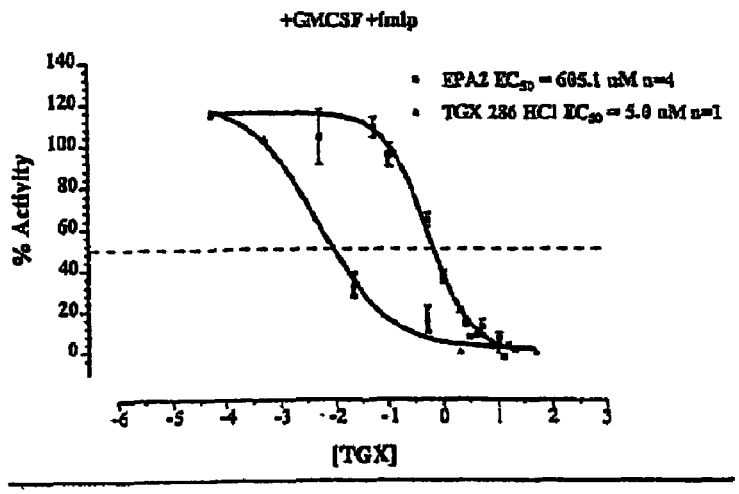
Figure 6B:
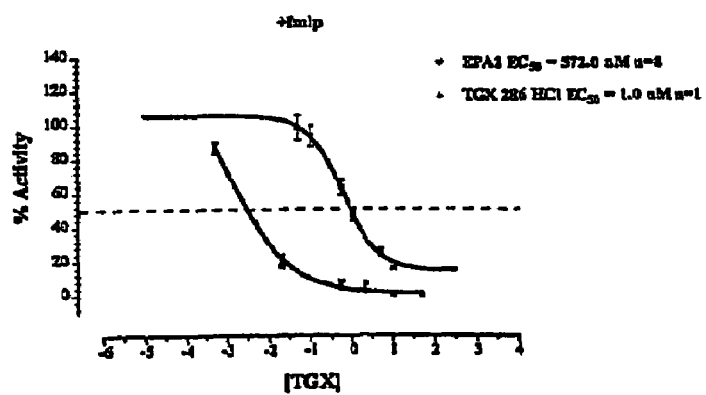

FIGS. 6A and 6B show the effect of various concentrations of TGX-286 on the ROS response.

Figure 7:
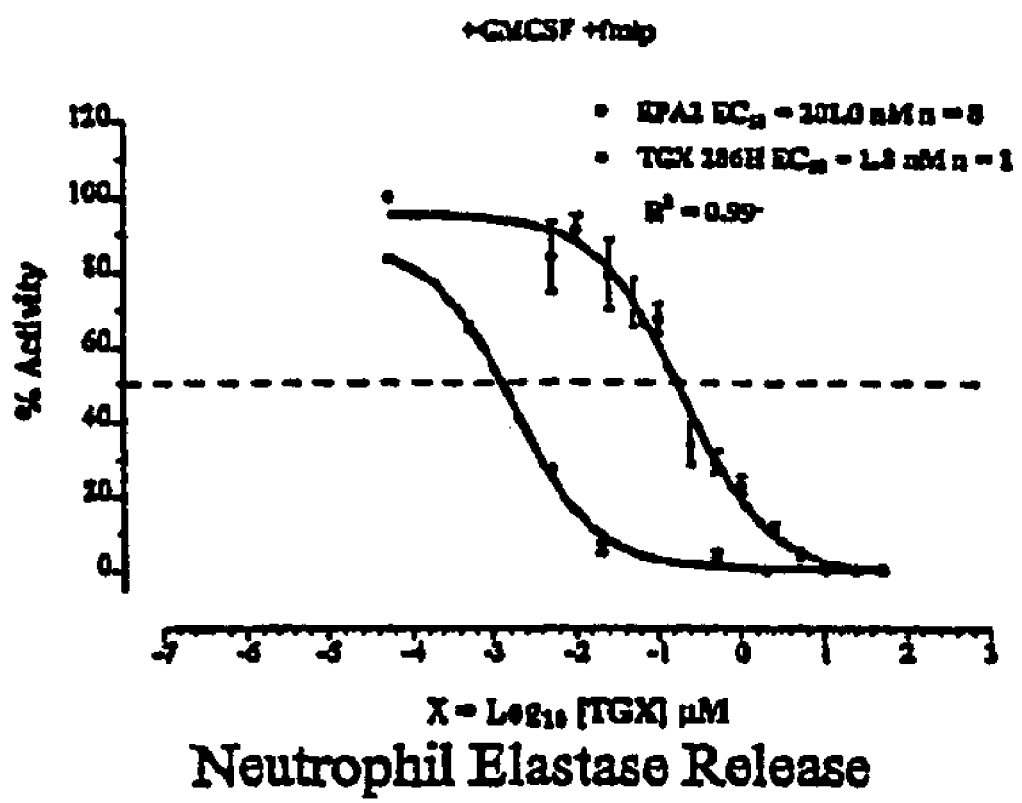

FIG. 7 shows the effect of various concentrations of TGX-286 on the elastase release.

DETAILED DESCRIPTION OF THE PREFERRED EMBODIMENT

The two major platelet adhesion receptors, GPIb/V/IX ("GPIb") and integrin $\alpha_{IIb}\beta_3$, possess unique mechano-sensory functions relevant to platelet activation under conditions of rheological disturbances (high shear and rapid accelerations in shear). The present inventors discovered that signaling through both receptors is regulated by rapid accelerations in shear rate ($\uparrow\Delta\gamma$), inducing platelet activation through PI 3-kinase-dependent signaling processes.

Thus, the present inventors have elucidated a critical signaling mechanism regulating platelet activation under high shear conditions and, consequently, have identified PI 3-kinase β as an element that induces platelet activation under pathological blood flow conditions. Existing anti-platelet therapies that block specific platelet adhesion receptors do not discriminate between pathological and normal haemostatic platelet activation. Therefore, the inventors' discovery, that selective inhibition of PI 3-kinase β can prevent platelet activation induced by pathological increases in shear rate, without affecting platelet activation induced by physiological agonists, provides a novel and specific approach to anti-thrombotic therapy, including new chemical compounds for such therapy.

Figure 1:
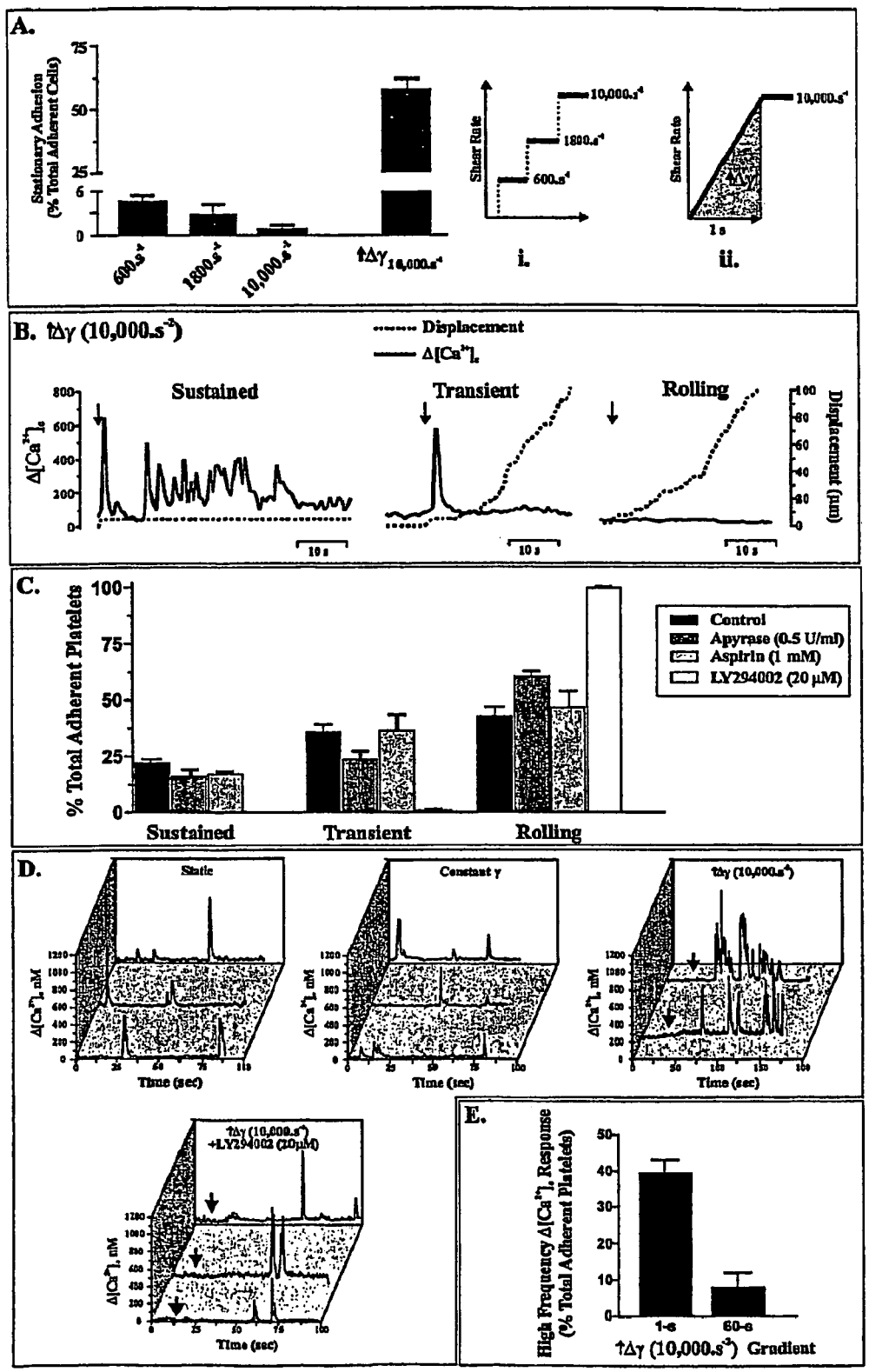
FIGS. 1A-1E represent results of tests for demonstrating that inhibition of PI 3-kinase by LY294002 or wortmannin eliminates platelet responses to accelerated shear. The use of an in vitro-flow based adhesion assay enables us to simultaneously analyze platelet adhesion dynamics and activation (by monitoring cytosolic calcium flux) on immobilized von Willebrand factor (vWf). Briefly, isolated platelets are perfused through vWf (100 μg/ml) coated microcapillary tubes and analysis of cytosolic calcium flux conducted in real-time by confocal microscopy.

As illustrated in FIG. 1A, the shear environment regulates activation and adhesion of platelets to vWf. In contrast to platelets exposed to steady state shear, exposure to accelerations in shear rate ($\uparrow\Delta\gamma$) results in more platelet activation and stationary adhesion contacts. Closer examination of platelet activation by monitoring cytosolic calcium flux revealed that $\uparrow\Delta\gamma$ had distinct, complimentary effects on GPIb and integrin $\alpha_{IIb}\beta_3$ calcium signaling. In the case of integrin $\alpha_{IIb}\beta_3$ calcium signaling, $\uparrow\Delta\gamma$ induced rapid-onset calcium signals that were specifically maintained in platelets able to remain firmly adhered to vWf. This shear-regulated integrin $\alpha_{IIb}\beta_3$ calcium signal occurred independently of endogenous platelet agonists (ADP and $TXA_2$), but was completely dependent on PI 3-kinase (FIGS. 1B and 1C). $\uparrow\Delta\gamma$ induced a novel GPIb calcium signal, distinct from the GPIb calcium transients that were previously recognized in Nesbit et al., 2002, *J. Biol. Chem.*, 277:2965. (FIG. 1D). The three defining characteristics of the $\uparrow\Delta\gamma$ GPIb calcium signal include (1) its strict dependence on the rate of acceleration of $\gamma$ (FIG. 1E), (2) the increased frequency of the calcium response (FIG. 1D), and (3) its sensitivity to PI 3-kinase inhibitors (FIG. 1D).

Because both GPIb and integrin $\alpha_{IIb}\beta_3$ calcium signaling depends on PI 3-kinase, inhibition of PI 3-kinase results in eliminating GPIb and integrin $\alpha_{IIb}\beta_3$ calcium signals triggered by the rapid acceleration of shear rate ($\uparrow\Delta\gamma$).

The initial study of the ability of the structurally unrelated PI 3-kinase inhibitors, such as LY294002 or wortmannin (see below), to prevent shear-induced platelet aggregation suggested an important mechano-sensory signaling function for PI 3-kinase for shear-induced platelet activation. In as much as these compounds do not distinguish among the various isoforms of PI 3-kinases, however, it remained unclear which particular PI 3-kinase isoform or isoforms are involved in shear-dependent platelet activation.

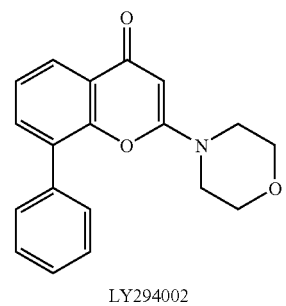

LY294002

-continued

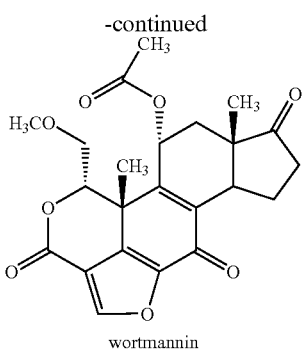

wortmannin

Illustrative compounds of the present invention that selectively inhibit PI 3 kinase β are shown below:

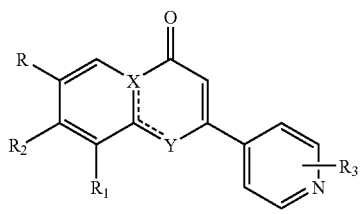
(I)

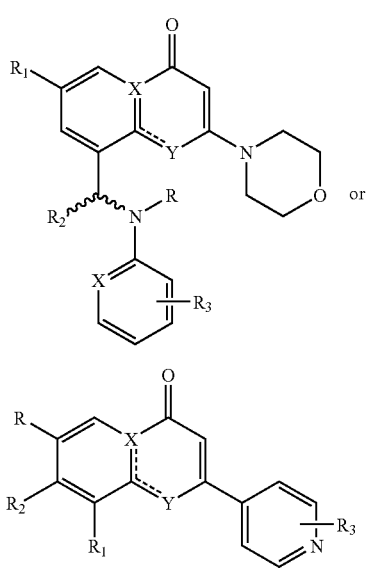
(III)

The 2-morpholino-substituted derivatives of formula (I) are defined below:

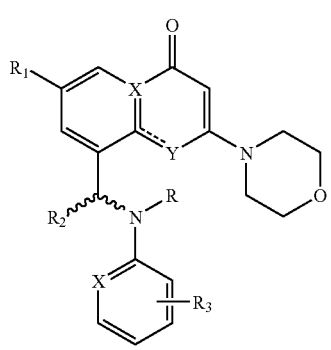
(I)

wherein,

X is C or N; Y is N or O;

R is H, $C_1$-$C_6$ branched or straight chain alkyl, or aryl or $(CH_2)_n$-aryl;

$R_1$ is H, OH, $OCH_3$, $OCF_3$, F, Cl, $CF_3$, $C_1$-$C_6$ branched or straight chain alkyl, or aryl or $(CH_2)_n$-aryl;

$R_2$ is H, $C_1$-$C_6$ branched or straight chain alkyl, or aryl or $(CH_2)_n$-aryl in either the R or the S configuration;

$R_3$ is one or more of H, F, Cl, Br, I, CN, $CO_2H$, $CO_2R$, $NO_2$, $CF_3$, substituted or unsubstituted $C_1$-$C_6$ alkyl, substituted or unsubstituted cycloalkyl, substituted or unsubstituted aryl, $OCH_3$, $OCH_2F$, $OCHF_2$, $OCF_3$, OR, $OSO_2$-aryl, substituted or unsubstituted amine, NHCOR, $NHSO_2R$, CONHR, or $SO_2NHR$.

In addition to the compounds of Formula (I) as inhibitors of PI 3-kinase β activity, novel compounds of Formula (III) which selectively inhibit PI 3-kinase β are defined:

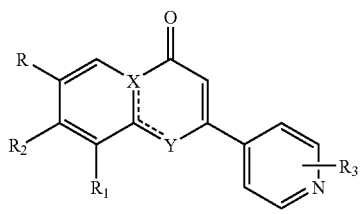
(III)

where X and Y are C and O respectively, or C and NH respectively, or both N.

R is H, OH, $OCH_3$, $OCF_3$, F, Cl, Br, I, $C_1$-$C_6$ alkyl, aryl or $(CH_2)_n$-aryl;

$R_1$, $R_2$ and $R_3$ are independently H, OH, F, Cl, Br, I, $C_1$-$C_6$ alkyl, $C_3$-$C_6$ cycloalkyl, CH=CH-aryl, C≡C-aryl, $(CHR^{t3})_n$-aryl, $NR^{t3}$—$C_1$-$C_6$ alkyl, $NR^{t3}$-cycloalkyl, $NR'_3$—$(CHR'_3)_n$-aryl, $(CHR^{t3})_n$—$NR^{t3}$-aryl, $(CHR^{t3})_n$—$NR^{t3}$-alkyl, $(CHR^{t3})_n$—$NR^{t3}$-cycloalkyl, $(CHR^{t3})_n$—O-aryl, $(CHR^{t3})_n$—O-alkyl, $(CHR^{t3})_n$—O-cycloalkyl, O—$(CHR^{t3})_n$-aryl, S—$(CHR^{t3})_n$-aryl, or CO-aryl, wherein n is 0,1, or 2 and alkyl, cycloalkyl or aryl is optionally substituted with F, Cl, Br, I, CN, $CO_2H$, $CO_2R^{t3}$, $NO_2$, $CF_3$, substituted or unsubstituted $C_1$-$C_6$ alkyl, substituted or unsubstituted cycloalkyl, substituted or unsubstituted aryl, $OCF_3$, $OR^{t3}$, $OSO_2$-aryl, substituted or unsubstituted amine, $NHCOR^{t3}$, $NHSO_2R^{t3}$, $CONHR^{t3}$, or $SO_2NHR^{t3}$; and $R^{t3}$ is H, or substituted or unsubstituted $C_1$-$C_6$ alkyl, substituted or unsubstituted aryl.

Preferred compounds useful for the methods of the present invention includes the 2-morpholino-substituted pyridopyrimidine derivatives of formula (I) wherein R is H, $C_1$-$C_6$ branched or straight chain alkyl or aryl;

$R_1$ is H, OH, $OCH_3$, $OCF_3$, F, Cl, $CF_3$, $C_1$-$C_6$ branched or straight chain alkyl;

$R_2$ is H, $C_1$-$C_6$ branched or straight chain alkyl, or aryl in either the R or the S configuration $R_3$ is one or more of H, F, Cl, Br, CN, $CO_2H$, $CO_2R$, $NO_2$, $CF_3$, branched or straight chain $C_1$-$C_6$ alkyl, substituted or unsubstituted cycloalkyl, substituted or unsubstituted aryl, $OCH_3$, $OCH_2F$, $OCHF_2$, $OCF_3$, OR, substituted or unsubstituted amine, NHCOR, $NHSO_2R$, CONHR, or $SO_2NHR$ X is C or N and Y is C or O.

Examples of some specific inhibitors according to Formula (I) include:

(±)-7-methyl-9-{[methyl(phenyl)amino]methyl}-2-morpholin-4-yl-pyrido[1,2-a]pyrimidin-4-one (TGX-195);

(±)-7-methyl-2-morpholin-4-yl-9-(1-phenylaminoethyl)-pyrido[1,2-a]pyrimidin-4-one (TGX-221);

(±)-9-[1-(3,5-difluorophenylamino)ethyl]-7-methyl-2-morpholin-4-yl-pyrido[1,2-a]pyrimidin4-one (TGX-239);

(±)-9-[1-(4-chlorophenylamino)ethyl]-7-methyl-2-morpholin-4-yl-pyrido[1,2-a]pyrimidin-4-one (TGX-243);

(±)-9-[1-(3,4-dichlorophenylamino)ethyl]-7-methyl-2-morpholin-4-yl-pyrido[1,2-a]pyrimidin-4-one (TGX-244);

(±)-9-[1-(3-chlorophenylamino)ethyl]-7-methyl-2-morpholin-4-yl-pyrido[1,2-a]pyrimidin-4-one (TGX-248);

(±)-7-methyl-9-[1-(3-methylphenylamino)ethyl]-2-morpholin4-yl-pyrido[1,2-a]pyrimidin-4-one (TGX-262);

(±)-7-methyl-2-morpholin-4-yl-9-[1-(3-trifluoromethylphenylamino)ethyl]-pyrido[1,2-a]pyrimidin-4-one (TGX-264); and (±)-7-methyl-2-morpholin-4-yl-9-[1-(2-pyridinylamino)ethyl]-pyrido[1,2-a]pyrimidin-4-one (TGX-295).

In the context of this description, the term "alkyl" refers to straight or branched saturated aliphatic hydrocarbon radical. Preferably, the alkyl group has 1 to 6 carbons as exemplified by methyl, ethyl, propyl, isopropyl, butyl, isobutyl, sec-butyl, t-butyl, pentyl, i-pentyl, hexyl and the like. The alkyl group is optionally substituted with one or more groups selected from halogen such as F, Cl, Br or I; CN; $CO_2R_3$; $NO_2$; $CF_3$; substituted or unsubstituted $C_1$-$C_6$ alkyl; substituted or unsubstituted $C_3$-$C_6$ cycloalkyl; substituted or unsubstituted aryl; $OCF_3$, $OR_3$, substituted or unsubstituted amine; $NHCOR_3$; $NHSO_2R_3$; $CONHR_3$; or $SO_2NHR_3$, wherein $R_3$ is H, substituted or unsubstituted $C_1$-$C_6$ alkyl, substituted or unsubstituted aryl.

The term "cycloalkyl" refers to non-heterocyclic (i.e., carbocyclic) or heterocyclic ring. Exemplary of non-heterocyclic ring in this regard is substituted or unsubstituted cyclopropane, cyclobutane, cyclopentane, cyclohexane, cyclohexadione, cyclopentanedione, quinone and the like. Suitable heterocycloalkyl groups include substituted or unsubstituted pyrrolidine, piperidine, piperazine, 2-piperidone, azacyclohexan-2-one and morpholine groups. The cycloalkyl group is optionally substituted at one or more positions with halogen such as F, Cl, Br or I; CN; $CO_2R_3$; $NO_2$; $CF_3$, substituted or unsubstituted $C_1$-$C_6$ alkyl; substituted or unsubstituted $C_3$-$C_6$ cycloalkyl; substituted or unsubstituted aryl; $OCF_3$, $OR_3$, substituted or unsubstituted amine; $NHCOR_3$; $NHSO_2R_3$; $CONHR_3$; or $SO_2NHR_3$, wherein $R_3$ is H, substituted or unsubstituted $C_1$-$C_6$ alkyl, substituted or unsubstituted aryl.

The term "aryl" refers to an aromatic or heteroaromatic rings. Examples of an aryl group are pyrrolidine, thiophene, pyrrole, pyrazole, imidazole, 1,2,3-triazole, 1,2,4-triazole, oxazole, isoxazole, thiazole, isothiazole, furan, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, tetrazole, benzene, pyridine, pyridazine, pyrimidine, pyrazine, triazine, indene, naphthalene, indole, isoindole, indolizine, benzofuran, benzothiophene, indazole, benzimidazole, benzthiazole, purine, quinolizine, quinoline, isoquinoline, cinnoline, phthalazine, quinazoline, quinoxaline, naphthyridine, pteridine, fluorene, carbazole, carboline, acridine, phenazine, and anthracene. The aryl group is optionally substituted at one or more positions with halogen such as F, Cl, Br or I; CN; $CO_2R_3$; $NO_2$; $CF_3$, substituted or unsubstituted $C_1$-$C_6$ alkyl; substituted or unsubstituted $C_3$-$C_6$ cycloalkyl; substituted or unsubstituted aryl; $OCF_3$, $OR_3$, substituted or unsubstituted amine; $NHCOR_3$; $NHSO_2R_3$; $CONHR_3$; or $SO_2NHR_3$, wherein $R_3$ is H, substituted or unsubstituted $C_1$-$C_6$ alkyl, substituted or unsubstituted aryl.

The term "selective PI 3-kinase β inhibitor" as used herein refers to a compound that inhibits PI 3-kinase β at least ≧10-fold, preferably ≧20-fold, more preferably ≧30-fold more effectively than other isoforms of the PI 3-kinase family. A "selective PI 3-kinase β inhibitor" compound is understood to be more selective for PI 3-kinase β than compounds conventionally and generally designated PI 3-kinase inhibitors such as LY294002 or wortmannin. Compounds of any type that selectively inhibit PI 3-kinase β expression or activity can be used as selective PI 3-kinase β inhibitors in the methods of the present invention.

The pyridine-substituted compounds of the present invention have been found to inhibit the lipid signaling enzyme PI 3-kinase, which regulates platelet-adhesion processes under high shear blood-flow conditions, and therefore to display anti-thrombotic activity, as well as other pharmacological properties elaborated below. PI 3-kinase generates 3-phosphorylated PI second messengers, including phosphatidylinositol-3-phosphate (PI(3)P), phosphatidylinositol-3,4-bisphosphate (PI(3,4)$P_2$), and phosphatidylinositol-3,4,5-triphosphate (PI(3,4,5)P3). These second messengers are thought to regulate a diverse range of cellular phenomena, including glucose transport, apoptosis prevention, vesicular trafficking, cell growth, and cytoskeletal reorganization.

There are no published reports on the effects of PI 3-kinase inhibitors on platelet adhesion under pathophysiologically relevant flow conditions. Nevertheless, it has been discovered that PI 3-kinase plays a critical role in regulating platelet adhesion, particularly under conditions of physiological flow. Thus, treatment of platelets with the compounds of the present invention inhibit the formation of the phosphorylated lipid products of PI 3-kinase, PI(3)P, PI(3,4)$P_2$, and PI(3,4,5) $P_3$, effecting a marked reduction in platelet adhesion to a vWf matrix under flow conditions. This reduction in platelet adhesion is associated with abnormal platelet spreading and thrombus formation. Because shear-dependent platelet adhesion and activation is important in arterial thrombus formation, PI 3-kinase is an important target for therapeutic intervention in cardiovascular diseases generally.

These inhibitors of PI 3-kinase also have potential therapeutic uses in a variety of other disease states. For example, PI 3-kinase plays an important role in promoting smooth muscle proliferation in the vascular tree, i.e., vascular smooth muscle cells, Thyberg, 1998, *European Journal of Cell Biology* 76(1):33-42, and in the lungs (airway smooth muscle cells). Krymskaya et al., 1999, *American Journal of Physiology* 277:65-78. Excessive proliferation of vascular smooth muscle cells plays an important role in the formation of atherosclerotic plaques and in the development of neointimal hyperplasia following invasive vascular procedures. Scwartz et al., 1984, *Progress in Cardiovascular Disease* 26:355-372; Clowes et al., 1978, *Laboratory Investigations* 39:141-150. Moreover, excessive proliferation of airway smooth muscle cells leads to the development of COPD in the setting of asthma and chronic bronchitis. Inhibitors of PI 3-kinase therefore may be used to prevent vascular restenosis, atherosclerosis, and COPD.

PI 3-kinase also plays an important role in regulating tumor cells and in the propensity of these cells to undergo apoptosis growth. Sellers et al., 1999, *The Journal of Clinical Investigation* 104:1655-1661. Additionally, uncontrolled regulation of the PI 3-kinase lipid products PI(3,4,5)$P_3$ and PI(3,4)$P_2$ by the lipid phosphatase PTEN plays an important role in progression of a number of malignant tumors in humans. Leevers et al., 1999, *Current Opinion in Cell Biology* 11:219-225. Therefore, inhibitors of PI 3-kinase may be used to treat neoplasms in humans.

PI 3-kinase also plays an important role in leukocyte function (Fuller et al., 1999, *The Journal of Immunology* 162(11): 6337-6340; Eder et al., 1998, *The Journal of Biological*

Chemistry 273(43):28025-31) and lymphocyte function (Vicente-Manzanares et al., 1999, *The Journal of Immunology* 163(7):4001-4012). For example, leukocyte adhesion to inflamed endothelium involves activation of endogenous leukocyte integrins by a PI 3-kinase-dependent signaling process. Furthermore, oxidative burst (Nishioka et al., 1998, *FEBS Letters* 441(1):63-66) and cytoskeletal reorganization (Kirsch et al., 1999, *Proceedings National Academy of Sciences USA* 96(11):6211-6216) in neutrophils appears to involve PI 3-kinase signaling. Thus, inhibitors of PI 3-kinase may be useful in reducing leukocyte adhesion and activation at sites of inflammation and therefore may be used to treat acute and/or chronic inflammatory disorders. PI 3-kinase also plays an important role in lymphocyte proliferation and activation. Fruman et al., 1999, *Science* 283 (5400):393-397. Given the important role of lymphocytes in auto-immune diseases, inhibitors of PI 3-kinase may be used in the treatment of such disorders.

The relative efficacies of compounds as inhibitors of an enzyme activity can be established, for example, by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$." $IC_{50}$ can be determined using conventional techniques known in the art.

It has been identified, in accordance with the instant invention, that PI 3-kinase β in platelets possesses a key mechano-sensory function relevant to shear-induced platelet activation and occlusive thrombus formation. Analysis of the effects of a PI 3-kinase β inhibitor, TGX-221, on mechano-transduction through GPIb and integrin $\alpha_{IIb}\beta_3$ demonstrated an absolute requirement for PI 3-kinase β for ↑Δγ induced calcium flux through both receptors (FIGS. 4A and 4B). The effects of TGX-221 on calcium flux were shear selective, as it did not inhibit the γ-independent GPIb calcium signalling (FIG. 4B). Furthermore, other platelet activation responses, such as integrin $\alpha_{IIb}\beta_3$ activation (PAC-1 binding) and α-granule secretion (P-selectin expression), induced by thrombin, collagen and ADP were unaffected by TGX-221 (FIG. 4C).

The signaling function of PI 3-kinase β operates downstream of the two major platelet adhesion receptors, GPIb and integrin $\alpha_{IIb}\beta_3$, to promote cytosolic calcium flux and platelet activation under conditions of rheological disturbance. Due to the mechano-sensory function of these receptors, inhibition of PI 3-kinase β eliminates occlusive thrombus formation without interfering with the normal platelet functional responses required for haemostasis.

To investigate the antithrombotic potential of the present compounds, two distinct thrombosis models were utilised; a modified Folts model in rats and rabbits (Folts et al., 1991, Circulation, IV-3-IV-14) and an electrolytic injury carotid model in rats (Bush et al., 1990, Faseb J., 4:3087). Infusion of the experimental animals with 2 mg/kg of an inventive compound, e.g., TGX-221, completely prevented occlusive thrombus formation in both models (FIGS. 5A and 5B) while preserving carotid blood flow volume over the 60 min post-injury period (FIG. 5B insert). Further, TGX-221 had no effect on baseline arterial blood pressure, heart rate or blood flow in the injured carotid artery in both the Folts and electrolytic studies (data not shown). Significantly, TGX-221 treatment did not adversely impact on normal haemostasis in these animals, as assessed by tail or ear bleeding times or, prolong the bleeding caused by other anticoagulants such as heparin, asprin or clopidogrel when administered in combination (FIG. 5C).

The invention outlined here defines a key mechano-sensory function for PI 3-kinase β in platelets, relevant to shear-induced platelet activation and occlusive thrombus formation. The demonstration that the PI 3-kinase β inhibitor, TGX-221 abolishes occlusive thrombus formation while not interfering with normal platelet functional responses associated with haemostasis defines this novel lipid kinase inhibitor as an important new agent for anti-thrombotic therapy.

Advantageously, in the present methods for preventing or treating a disease condition, the effective amount of one of the present compounds is administered in the form of a dose. In preferred embodiments, the dose is preferably in the form of a tablet (e.g., a tablet formulated for oral, sublingual, and buccal administration), capsule (e.g., a capsule containing powder, liquid, or a controlled-release formulation), intravenous formulation, intranasal formulation, formulation for muscular injection, syrup, suppository, aerosol, buccal formulation, transdermal formulation, or pessary. Preferably, the dose contains from about 5 to about 500 mg of the compound, and more preferably contains from about 25 to about 300 mg of the compound.

Another aspect of the present invention relates to a pharmaceutical composition containing a pyridine-substituted compound of the present invention together with one or more pharmaceutically acceptable carriers and/or diluents. Below, the term "active ingredient" may be any pyridine-substituted compound of the present invention, or a physiologically acceptable salt, solvate, or functional derivative thereof.

Administration of this pharmaceutical composition is performed by any convenient means. Doses are administered daily, weekly, monthly, or at other suitable time intervals such as by the oral, intravenous, intraperitoneal, intramuscular, subcutaneous, intradermal, or suppository routes, or by implanting (e.g. using slow-release molecules). If the active compound is administered in tablet form, the tablet contains a binder such as tragacanth, corn starch, or gelatin; a disintegrating agent, such as alginic acid; and a lubricant, such as magnesium stearate.

The pharmaceutical compositions suitable for injectable use include sterile aqueous solutions or dispersions, and sterile powders for the extemporaneous preparation of sterile injectable solutions or dispersions, or are in the form of a cream or other form suitable for topical application. The carrier can be a solvent or dispersion medium containing, for example, water, ethanol, polyol (e.g., glycerol, propylene glycol, and liquid polyethylene glycol, and the like), suitable mixtures thereof, and vegetable oils. The proper fluidity is maintained, for example, by the use of a coating such as lecithin, by the maintenance of the required particle size in the case of dispersion, and by the use of superfactants. Prevention of contamination by microorganisms can be brought about by various antibacterial and antifungal agents, for example, parabens, chlorobutanol, phenol, sorbic acid, thimerosal and the like. It may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, followed by filter sterilization. Generally, dispersions are prepared by incorporating the various sterilized active compounds into a sterile vehicle containing the basic dispersion medium and one or more of the above-described ingredients. In the case of sterile powders for the preparation of sterile injectable solutions, the preferred methods of preparation are vacuum drying and freeze drying which yield a powder of the active compound plus any additional desired ingredients from previously sterile-filtered solutions thereof.

The pharmaceutical compositions are orally administered, for example, with an inert diluent or with an assimilable edible carrier, are enclosed in hard or soft shell gelatin capsule, are compressed into tablets, or are incorporated directly with food. For oral administration, the active compounds are incorporated with excipients, and are used in the form of ingestible tablets, buccal tablets, troches, capsules, elixirs, suspensions, syrups, wafers, and the like. Such compositions and preparations contain at least 1% by weight of active compound. The percentage of the compositions and preparations may be varied and may be between about 5 to about 80% of the weight of the unit. The amount of active compound in such therapeutically useful compositions is such that a suitable dosage will be obtained.

The tablets, troches, pills, capsules and the like may also contain a binder such as gum, acacia, corn starch, or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The invention is further described by reference to the following examples, which are set forth by way of illustration only. Nothing in these examples should be taken as a limitation upon the overall scope of the invention.

SYNTHESIS EXAMPLES

Example 1

Synthesis of (±)-7-methyl-2-morpholin-4-yl-9-(1-phenylaminoethyl)-pyrido[1,2-a]-pyrimidin-4-one (TGX-221: $R_1$=$CH_3$, $R_2$=$CH_3$, $R_3$=H)

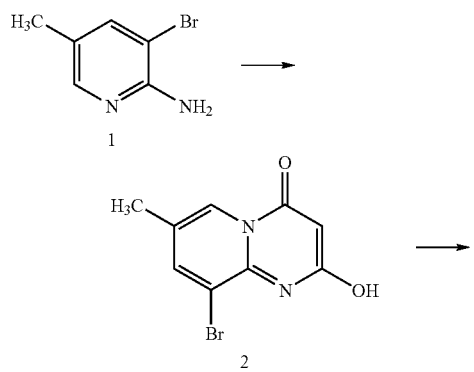

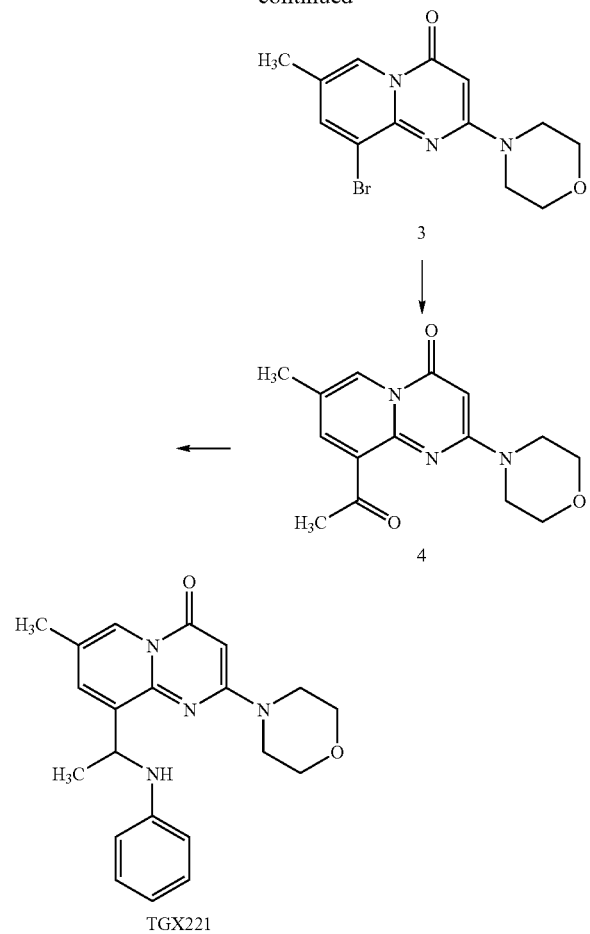

Compound 2: To a solution of 2-amino-3-bromo-5-methylpyridine (1) (45 g, 0.24 mol) in dichloromethane (500 mL) was added malonyl dichloride (25 mL, 0.25 mol) at ice-cold temperature. The mixture was then stirred at ambient temperature for 48 h. The precipitated light yellow solids were collected by filtration, washed with dichloromethane (3×100 mL) and dried under vacuum to afford product 2 (52.5 g). The filtrate was concentrated under reduced pressure. The resulting residue was suspended in $H_2O$ and stirred for 1 h. The solution was filtered and the filtrate was neutralized with solid $NaHCO_3$ to give unreacted 2-amino-3-bromo-5methylpyridine (6 g). The crude compound 2 was taken to next synthetic step without further purification. $^1$H NMR (300 MHz, DMSO-$d_6$) δ 8.72 (s, 1H), 8.28 (s, 1H), 5.50 (s, 1H), 2.33 (s, 3H).

Compound 3: To a suspension of compound 2 (12.75 g, 0.05 mol) in dichloromethane (300 mL) was added triethylamine (14 mL, 0.1 mol) followed by methanesulfonyl chloride (5.42 mL, 0.07 mol) at ice-cold temperature. The reaction mixture was then stirred for 0.5 h at room temperature. After the addition of morpholine (13 mL, 0.15 mol), the reaction mixture was stirred for 24 h at refluxing temperature. The mixture was concentrated under reduced pressure and diluted with $H_2O$ (300 mL) to afford a pale yellow precipitate. The solid was filtered and dried under reduce pressure and identified as the ketone 3 (6.8 g, >80% pure by HPLC). The product 3 was taken to next reaction sequence without further purification. ¹H NMR (300 MHz, CDCl₃) δ 8.69 (s, 1H), 7.84 (s, 1H), 5.58 (s, 1H), 3.80 (m, 4H), 3.70 (m, 4H), 2.32 (s, 3H).

Compound 4: To a solution of bromide 3 (35 mmol) in DMF (70 mL) was added, N,N-diisopropylethylamine (18 mL), butyl vinyl ether (13 mL) and dichloro 1,1'-bis(diphenylphosphino)ferrocene palladium(II) (1.09 g), 1.5 mmol). The suspension (became homogenous after 20 minutes) was then stirred at 120° C. for 16 h. The reaction mixture was cooled and poured into ice-cold solution of 1M HCl (200 mL) and stirred for 1 h. The solution was extracted with dichloromethane and the organic layer was washed with water, dried over Na₂SO₄ (*avoided washing with aqueous NaCl as the solution became an emulsion). After concentration in vacuo, the dark residue was purified by column chromatography (silica gel, 3:1 ethylacetate, petroleum ether) to give pale yellow solid. ¹H NMR (300 MHz, CDCl₃) δ 8.86 (s, 1H), 7.84 (s, 1H), 5.63 (s, 1H), 3.79 (m, 4H), 3.62 (m, 4H), 2.77 (s, 3H), 2.36 (s, 3H).

TGX221: To a suspension of ketone 4 (1 mmol) in toluene (10 mL) was added aniline (3 mmol) and refluxed for 4 h. The reaction mixture was gradually cooled and sodium borohydride (1 mmol) was added at ice-cold temperature. Then reaction mixture was further stirred for 1 h at room temperature. The solution was diluted with dichloromethane (30 mL), the organic layer was washed with water, brine and dried over Na₂SO₄. After concentration in vacuo, the residue was purified by column chromatography (silica gel, 3:1 ethylacetate, petroleum ether) to give pale yellow solid (>60% yield). ¹H NMR (300 MHz, CDCl₃) δ 8.65 (s, 1H), 7.58 (s, 1H), (7.11 br t, 2H), 6.68 (t, J=7.5 Hz, 1H), 6.46 (br t, 2H), 5.66 (s, 1H), 5.12 (m, 1H), 4.24 (br s, —NH, 1H), 3.80 (m, 4H), 3.68 (m, 4H), 2.26 (s, 3H), 1.57 (d, J=6.7 Hz, 3H).

Example 2

Preparation of Pyridine-Substituted Benzopyranone Derivatives 8-(Substituted)2-(4-pyridinyl)-4H-1-benzopyran-4-ones were prepared according to the following general procedure adapted from Cushman and Nagarathnam, 1990, *Tetrahedron Letters* 31: 6497. In brief, a variety of precursor 2-hydroxyacetophenones (1) were treated with the methyl ester of isonicotinic acid and derivatives followed by cyclodehydration to produced the pyridine substituted products (3). Specific substitutions at R₁ then were introduced by a variety of coupling reactions.

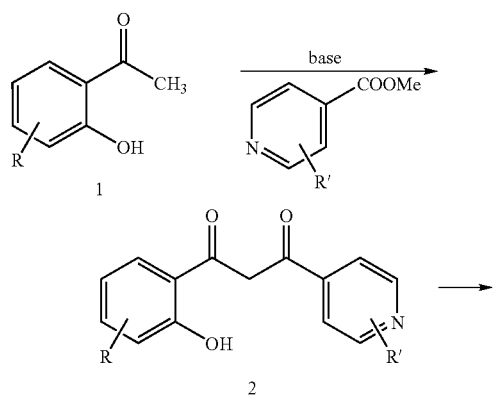

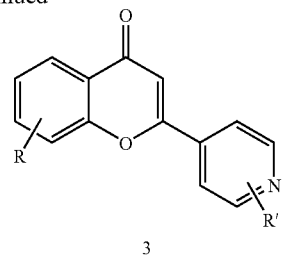

3

The substitution on acetophenone (R) may include, but is not restricted to bromo, hydroxy, acetamido, methoxymethyl, methyl, ethyl, methoxy, thrifluoromethanesulfonyloxy and acetyl substituents. The substitution on the isoniconate ester (R') includes but is not restricted to chloro, methyl and amino substituents. Reagents for the condensation reaction include the use of lithium bis(trimethylsilyl)amide, sodium hydride, 1,8-Diazabicyclo[2.2.2]undecane, potassium butoxide or sodium methoxide in solvents such as tetrahydrofuran or N,N-dimethylformamide. Cyclodehydration can be performed using reagent mixtures such as sulfuric acid in ethanol, hydrochloric acid in methanol, 1,8-diazabicyclo[2.2.2] undecane in DMF, triflouromethanesulfonic anhydride in dichloromethane.

Further reaction of the products (3) may include palladium catalysed cross-coupling reactions at R where R is a halide or trifluoromethanesulfonyloxy to yield products where R is aryl, arylamino, alkylamino or acetyl. Where R is an acetyl function, further reaction may include reduction or reductive amination to yield products where R is hydroxyethyl or aminoethyl. Where R is a methoxyalkyl or hydroxyalkyl function further reaction may yield products where R is bromoalkyl. Where R is bromoalkyl further reaction may yield products where R is arylaminoalkyl or aryloxyalkyl. Where R is hydroxy further reaction may yield products where R=aryloxy or alkyloxy. Where R is amino further reaction may yield products where R is arylamino or alkylamino.

The following examples further serve to illustrate the invention.

Preparation of Intermediates

Example 2a 6-methyl-8-acetyl-2-(4-pyridinyl)-4H-1-benzopyran-4-one

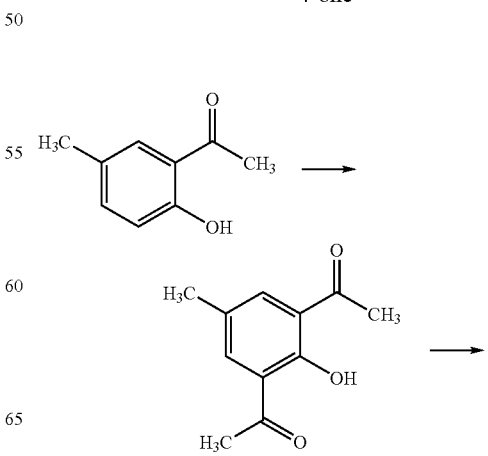

-continued

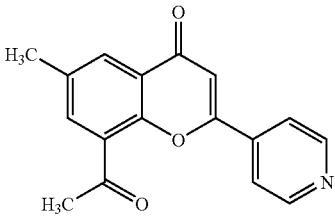

3'-acetyl-2'-hydroxy-5'-methylacetophenone

A mixture of 2-hydroxy-5-methylacetophenone (15 g, 0.1 mol) in dichloromethane (100 ml) was treated with triethylamine (13.9 ml), dimethaminopyridine (1.22 g) and acetic anhydride (9.5 ml) and stirred at room temperature overnight. The mixture was then poured into water (300 ml) and extracted with dichloromethane (3×60 ml). The combined extracts were washed with sat. aq. $NaHCO_3$, dried ($Na_2SO_4$) and the solvent removed to yield a colourless oil (19.5 g)

This product was dissolved in dichloromethane (200 ml) at 0° C. and treated with aluminium chloride (19.5 g) and stirred at room temperature for 5 days. The solution was treated with ice (50 g) and 2N hydrochloric acid (50 ml) and stirred at room temperature for 1 h. The dichloromethane layer was separated and the aqueous layer extracted with dichloromethane (2×60 ml). The combine extracts were washed with sat. aq. NaCl, dried ($Na_2SO_4$) and the solvent removed to yield the crude material. The product was purified by column chromatography (0-25% ethyl acetate in petrol) to yield a yellow/green solid (11.4 g)

8-acetyl-6-methyl-2-(4-pyridinyl)-4H-1-benzopyran-4-one

To a solution of 3'-acetyl-2'-hydroxy-5'-methylacetophenone (3.0 g, 15.6 mmol) in anhydrous THF (100 ml) at −78° C. under an atmosphere of nitrogen was added lithium bis(trimethylsilyl)amide (1.0M in THF, 50 ml, 50 mmol) and the mixture was allowed to stir at 0° C. for 1 h. The mixture was cooled to −78° C. and methyl isonicotinate (2.14 ml, 15.6 mmol) was added. The reaction mixture was allowed to warm to room temperature and stirring was continued overnight. The mixture was poured into a 1N hydrochloric acid solution (200 ml) and the THF was removed in vacuo. The mixture was neutralised with 1N aqueous sodium hydroxide, then filtered. The filter cake was dried under high vacuum overnight.

The resultant solid (3.0 g) was treated with acetic acid (40 ml) then conc. sulfuric acid (2 ml) and heated for 3 h at 80° C. Upon cooling the mixture was diluted with water (100 ml) and neutralised with 1N aq. sodium hydroxide. The precipitate was filtered, washed with water and dried under high vacuum. The crude product was purified by column chromatography, eluting with a gradient of 0-20% methanol in ethyl acetate to yield a tan solid.
ES-MS: 280.36 (M+H)

In a similar manner were also prepared:

8-hydroxy-2-(4-pyridinyl)-4H-1-benzopyran-4-one from 2,3-dihydroxyacetophenone; ES-MS: 240.2 (M+H);

8-bromo-6-methyl-2-(4-pyridinyl)-4H-1-benzopyran-4-one from 3-bromo-5-methyl-2-hydroxyacetophenone; ES-MS: 316.2, 318.2 (M+H);

7-hydroxy-2-(4-pyridinyl)-4H-1-benzopyran-4-one from 2,4-dihydroxyacetophenone; ES-MS: 240.15 (M+H);

8-acetylamino-2-(4-pyridinyl)-4H-1-benzopyran-4-one from 3-acetylamino-2-hydroxyacetophenone; ES-MS: 281.2 (M+H);

8-amino-2-(4-pyridinyl)-4H-1-benzopyran-4-one from 3-acetylamino-2-hydroxyacetophenone; ES-MS: 239.2 (M+H);

8-acetyl-6-methyl-2-(2-chloro-6-methyl-4-pyridinyl)-4H-1-benzopyran-4-one ES-MS: 328.12, 330.12 (M+H);

8-acetyl-6-methyl-2-(2-amino-4-pyridinyl)-4H-1-benzopyran-4-one ES-MS: 295.5 (M+H);

6-methyl-8-acetyl-2-(3-pyridinyl)-4H-1-benzopyran-4-one ES-MS: 280.3 (M+H); and 6-methoxy-8-methoxymethyl-2-(3-pyridinyl)-4H-1-benzopyran-4-one ES-MS: 316.2 (M+H).

Example 2b

Heck coupling of bromo-chromone 8-acetyl-6-methyl-2-(4-pyridinyl)-4H-1-benzopyran-4-one (Alternate Method)

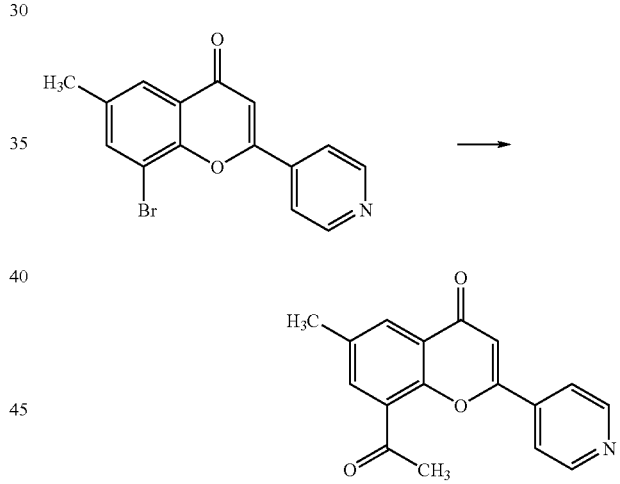

6-methyl-8-(acetyl)-2-(4-pyridinyl)-4H-1-benzopyran-4-one

A mixture of 8-bromo-2-(4-pyridinyl)-6-methyl-4H-1-benzopyran-4-one (0.12 g, 0.36 mmol), n-butyl vinyl ether (0.047 ml, 0.36 mmol), triethylamine (0.050 ml, 0.36 mmol) in DMF (5 ml) was purged with $N_2$ and then treated with $PdCl_2(dppf)$ (27 mg, 0.036 mmol). The mixture was heated to 90° C. overnight. The mixture was cooled to room temperature and treated with 1N aqueous HCl (30 ml) and stirring was continued overnight. The mixture was then diluted with water (50 ml), and lyophilized to dryness. The residue was eluted through a C8-HPLC column and the product isolated as an off-white solid (2.5 mg). The product was identical to that described above.

Example 2c

Reduction of acetylchromone 8-(1-hydroxyethyl)-2-(4-pyridinyl)-6-methyl-4H-1-benzopyran-4-one A mixture of 8-acetyl-6-methyl-2-(4-pyridinyl)-4H-1-benzopyran-4-one (4.6 g, 16.5 mmol) in methanol (100 ml) was treated with sodium borohydride (1.22 g, 33 mmol) and heated to reflux overnight. Upon cooling water (2 ml) was added and the solution concentrated to near-dryness in vacuo. Water (100 ml) was added and a precipitate formed which was filtered yielding a tan/orange solid (4.0 g).

Example 2d

Bromination of alcohol 8-(1-bromoethyl)-2-(4-pyridinyl)-6-methyl-4H-1-benzopyran-4-one A mixture of 8-(1-hydroxyethyl)-2-(4-pyridinyl)-6-methyl-4H-1-benzopyran-4-one (4.0 g) in glacial acetic acid (45 ml) was treated with 48% aqueous hydrobromic acid (34 ml) and heated at 80° C. overnight, upon cooling the mixture was poured into ice-cold water and neutralized with 50% sodium hydroxide and extracted with dichloromethane (3×40 ml). The combined extracts were dried and the solvent removed. The residue was chromatographed through a silica column eluting with 0-10% methanol in ethyl acetate to yield a tan solid (1.1 g). ESI-MS: 344.1, 346.1 (M+H) (Alternatively this product can be achieved by treatment of the alcohol with $PBr_3$ in dichloromethane).

Example 2e

Mesylation of alcohol 8-(1-methansulfonyloxyethyl)-2-(4-pyridinyl)-6-methyl-4H-1-benzopyran-4-one A mixture of 8-(1-hydroxyethyl)-2-(4-pyridinyl)-6-methyl-4H-1-benzopyran-4-one (2.4 g) in dichloromethane (100 ml) in an ice bath, was treated with triethylamine (1.3 ml) followed by methanesulfonylchloride (0.67 ml) and the mixture stirred at 0° C. for 30 minutes. The solution was then washed with 0.1N HCl (aq) (2×30 ml), dried (Na2SO4) and the solvent removed to yield a oily brown solid, which was not further purified.

Example 2f

Synthesis of 6-methyl-8-bromomethyl-2-(4-pyridinyl)-4H-benzopyran-1-one 6-methyl-8-bromomethyl-2-(4-pyridinyl)-4H-benzopyran-1-one

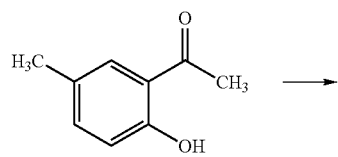

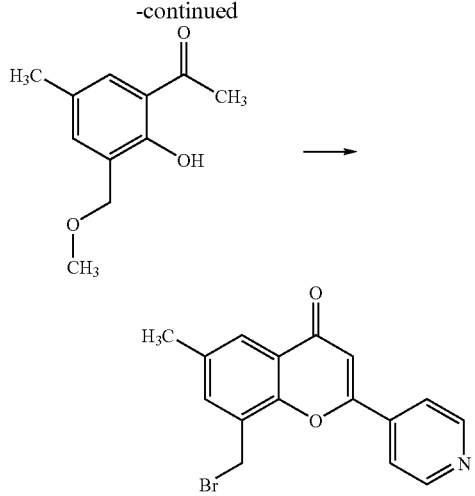

2'-hydroxy-5'-methyl-3'-methoxymethylacetophenone

A mixture of 2'-hydroxy-5'-methylacetophenone (1.0 g, 6.7 mmol) was treated with paraformaldehyde (0.18 g) and conc. hydrochloric acid (5 ml) and the mixture heated at 60° C. overnight. Upon cooling the mixture was extracted with toluene (3×30 ml) and the combined extracts were dried ($Na_2SO_4$) and the solvent removed to yield a yellow oil. The oil was treated with methanol (30 ml) and heated to reflux for 1 h. Upon cooling, the solution was evaporated to near dryness, and the residue chromatographed on a silica column, eluting with 0-10% ethyl acetate in petroleum ether. The purified product was obtained as an white powder (0.76 g)

8-bromomethyl-6-methyl-2-(4-pyridinyl)-4H-benzopyran-1-one

To a solution of the acetophenone (0.76 g, 3.9 mmol) in THF (30 ml) at −78° C. was added lithium bis(trimethylsilyl)amide (1.0M in THF, 11.8 ml, 11.8 mmol) and the mixture was allowed to stir at 0° C. for 1 h. The mixture was cooled to −78° C. and methyl isonicotinate (0.53 ml, 3.9 mmol) was added. The reaction mixture was allowed to warm to room temperature and stirring was continued overnight. The mixture was poured into a 1N hydrochloric acid solution (200 ml) and the THF was removed in vacuo. The mixture was neutralised with 1N aqueous sodium hydroxide, then filtered. The filter cake was dried under high vacuum overnight.

The residue was treated with acetic acid (6 ml) followed by hydrobromic acid (48% in water, 6 ml) and the mixture heated at 80° C. overnight. Upon cooling the mixture was taken to pH 5 with 2N sodium hydroxide solution. The resulting precipitate was filtered, and dried under vacuum. The residue was chromatographed through a silica column, eluting with 0-5% methanol in ethyl acetate. The product was isolated as an off white solid (310 mg).

LC-MS: 332,334 (M+H)

Example 2g

8-trifluoromethanesulfonyloxy-2-(4-pyridinyl)-4H-1-benzopyran-4-one

To a mixture of 8-hydroxy-2-(4-pyridinyl)-4H-1-benzopyran4-one (10 mg) in acetonitrile (2 ml) was added diisopropylethylamine (20 uL) followed by N-phenyltriflimide (20 mg), and the mixture stirred at room temperature for 2 h. The mixture adsorbed onto silica gel and was eluted through a silica column using ethyl acetate as eluant to yield the title compound as a tan solid. (10 mg). ESI-MS: 372.1 (M+H).

Example 2h

Reductive amination of ketone 8-1-(phenylamino)ethyl-6-methyl-2-(4-pyridinyl)-4H-1-benzopyran-4-one (TGX-286)

To a suspension of 8-acetyl-6-methyl-2-(4-pyridinyl)-4H-1-benzopyran-4-one (0.28 g) in methanol (30 ml) was added glacial acetic acid (2.5 ml), aniline (2.5 ml) and sodium cyanoborohydride (62 mg) and the mixture was heated at 70° C. overnight. Upon cooling the mixture was adsorbed onto silica gel and purified by column chromatography, eluting with a gradient of 0-10% methanol in ethyl acetate to yield a tan solid. (200 mg)

1H NMR ($CDCl_3$, 300 MHz): δ1.65 (d, 3H, J=1.2 Hz), 2.39 (s, 3H), 5.186 (m, 1H), 6.51 (d, 2H, J=7.8 Hz), 6.69 (t, 1H, J=7.5 Hz), 6.94 (s, 1H), 7.11 (t, J=8.1 Hz), 7.65 (d, 1H, J=1.8 Hz), 7.73 (d, 2H, J=6 Hz), 7.90 (s, 1H), 8.80 (d, 2H, J=6 Hz).

ES-MS: 357.3 (M+H), 264.3.

In a similar manner also were prepared:

8-1-(4-fluoro-2-methylphenylamino)ethyl-6-methyl-2-(4-pyridinyl)-4H-1-benzopyran-4-one (KN-303); ES-MS: 389.3 (M+B)

8-1-(phenylamino)ethyl-6-methyl-2-(3-pyridinyl)-4H-1-benzopyran4-one (KN-305); ES-MS 357.3 (M+H)

8-1-(6-methylpyridin-2-ylamino)ethyl-6-methyl-2-(4-pyridinyl)-4H-1-benzopyran-4-one (KN-310); ES-MS: 372.3 (M+B)

8-1-(3-trifluoromethylphenylamino)ethyl-6-methyl-2-(4-pyridinyl)-4H-1-benzopyran-4-one (KN-322); ES-MS: 425.0 (M+H)

8-1-(phenylamino)ethyl-6-methyl-2-(2-chloro-6-methyl-4-pyridinyl)-4H-1-benzopyran-4-one (KN-340); ES-MS: 405.44, 407.42 (M+H)

Example 2i

Reaction of bromomalkyl substituted chromones with phenols or anilines 6-methyl-8-phenylaminomethyl-2-(4-pyridinyl)-4H-benzopyran-1-one (KN-312)

A mixture of 8-bromomethyl-6-methyl-2-(4-pyridinyl)-4H-benzopyran-1-one (48 mg, 0.15 mmol) in acetonitrile (5 ml) was treated with aniline (48 uL, 0.52 mmol) and the mixture was heated at 70° C. for 4 h. Upon cooling the mixture was treated with solid potassium carbonate (60 mg), and the mixture was adsorbed onto silica gel (1.0 g), and the solvent removed. The residue was applied to a silica gel column and the product was eluted with 0-5% methanol in ethyl acetate. The product was isolated as a yellow powder (25 mg).

1H NMR ($CDCl_3$, 300 MHz): δ2.41 (s, 3H), 4.19 (s, 1H), 4.71 (s, 2H), 6.68 (d, 2H, J=8.4 Hz), 6.77 (t, 1H, J=7.2 Hz), 6.9 (s, 1H), 7.21 (t, 2H, 7.5 Hz), 7.59 (s, 1H), 7.67 (d, 2H, 4.8 Hz), 7.91 (s, 1H), 8.74 (s, 2H).

LC-MS: 343.08 (M+H), 249.98

In a similar manner were prepared:

6-methyl-8-phenoxymethyl-2-(4-pyridinyl)-4H-benzopyran-1-one (KN-313) ES-MS 344.1

6-methyl-8-(2-pyridinyl)aminomethyl-2-(4-pyridinyl)-4H-benzopyran-1-one (KN-315) ES-MS: 344.1

6-methyl-8-1-(phenoxy)ethyl-2-(4-pyridinyl)-4H-benzopyran-1-one (KN-317) ES-MS 358.1

6-methyl-8-(2-carboxy)phenylaminomethyl-2-(4-pyridinyl)-4H-benzopyran-1-one (KN-323) ES-MS 387.04 (M+H)

6-methyl-8-(2-acetamido)phenylaminomethyl-2-(4-pyridinyl)-4H-benzopyran-1-one (KN-326) ES-MS: 413.9 (M+H)

6-methyl-8-[1-(2-carboxy)phenylamino]ethyl-2-(4-pyridinyl)-4H-benzopyran-1-one (KN-334) ES-MS: 401.4

Example 2j 8-(1-(2-aminophenylamino)ethyl-2-(4-pyridinyl)-4H-benzopyran-1-one (KN327)

A mixture of 8-(1-methanesulfonyloxy)ethyl-6-methyl-2-(4-pyridinyl)-4H-benzopyran-1-one (2.4 g) in acetonitrile (50 ml) was treated with potassium carbonate (2.4 g) and mono-Boc phenylenediamine (2.7 g) and the mixture was heated at 70° C. overnight. Upon cooling the mixture was treated with dichloromethane and adsorbed onto silica gel. The solvent was removed and the residue was applied to a silica gel column and the product was eluted with 0-5% methanol in ethyl acetate. The product was isolated as a yellow oil (0.9 g).

ES-MS: 472.3 (M+H)

8-(1-(Boc-2-aminophenylamino)ethyl-2-(4-pyridinyl)-4H-benzopyran-1-one (0.9 g) in dichloromethane (12 ml) was treated with trifluoroacetic acid (8 ml) and the mixture stirred at room temp. for 1 h. The mixture was diluted with dichloromethane (30 ml) and extracted with water (30 ml) then 1N aq. hydrochloric acid (30 ml). The combined aqueous extracts were neatralised with aqueous sodium hydroxide solution, and extracted with dichloromethane (3×50 ml). The combine organic extracts were then re-extracted with 0.3N aqueous hydrochloric acid. (2×50 ml). The combine aqueous extracts were then lyophilized to dryness, yielding a red-brown solid (0.61 g).

ES-MS: 372.3

In a similar manner was prepared:

6-methyl-8-1-(2-trifluoromethyl-benzimidazol-1-yl)-ethyl-2-(4-pyridinyl)-4H-benzopyran-1-one (KN-328) ES-MS: 450 (M+H)

Example 2k

8-Benzyloxy-2-(4-pyridinyl)-4H-benzopyran-1-one (KN-335)

A mixture of 8-hydroxy-2-4-pyridinyl)-4H-benzopyran-1-one (52 mg) and anhydrous potassium carbonate (117 mg) in acetonitrile was treated with benzyl bromide and heated to reflux overnight. Upon cooling the mixture was treated with dichloromethane, adsorbed on silica gel and applied to a silica chromatography column. The products were eluted with 0-4% methanol in ethyl acetate, and the desired product was isolated as a brown solid (17 mg).

ES-MS: 330.2 (M+H)

In a similar manner was prepared:

7-Benzyloxy-2-(4-pyridinyl)-4H-benzopyran-1-one (KN-342) ES-MS: 330.5 (M+H)

Example 2l

8-Benzylamino-2-4-pyridinyl)-4H-benzopyran-1-one (KN-336)

A mixture of 8-amino-2-(4-pyridinyl)-4H-benzopyran-1-one (16 mg), benzaldehyde (40 µL), and acetic acid (20 µL), in methanol (5 ml) was treated with sodium cyanoborohydride (5 mg) and heated at 70° C. overnight. Upon cooling the solution was adsorbed onto silica gel and chromatographed through silica using a gradient of 0-5% methanol in ethyl acetate. The desired product was isolated as a yellow solid.

ES-MS: 329.3 (M+H)

Example 2m

8-Phenylamino-2-4-pyridinyl)-4H-benzopyran-1-one (KN-341)

A mixture of 8-amino-2-(4-pyridinyl)-4H-benzopyran-1-one (20 mg), phenylboronic acid 30 mg, 0.25 mmol), and triethylamine (70 uL, 0.5 mmol) in dichloromethane (5 ml) was treated with cupric acetate (45 mg, 0.25 mmol) and the mixture stirred at room temperature overnight. The mixture was then adsorbed onto silica and applied to a silica column and eluted with 0-5% methanol in ethyl acetate. The desired compound was obtained as a yellow solid (4 mg).

ES-MS: 315.5 (M+H).

In a similar manner was prepared:

8-(3-Fluorophenylamino)-2-(4-pyridinyl)-4H-benzopyran-1-one (KN-351) ES-MS: 333.3 (M+H)

Example 2n

8-Phenyl-6-methyl-2-(4-pyridinyl)-4H-benzopyran-1-one (TGX-258)

A nitrogen purged mixture of 8-bromo-6-methyl-2-(4-pyridinyl)-4H-benzopyran-1-one (0.1 g, 0.32 mmol), potassium phosphate (0.2 g, 0.95 mmol), phenylboronic acid (0.042 g, 0.35 mmol) and PdCl$_2$(dppf) (7.8 mg, 0.009 mmol) in dioxane (6 ml) was heated to reflux overnight. Upon cooling the mixture was filtered, and the filtrate concentrated to dryness. The residue was chromatographed through a C8 HPLC column using 0-60% acetonitrile in 0.1% aq. TFA as eluent. The purified fractions were combined to yield a yellow powder (53.4 mg).

1H NMR (CDCl$_3$, 300 MHz): δ2.53 (s, 3H), 7.03 (s, 1H), 7.55 (m, 6H), 7.80 (d, J=5.7 Hz, 2H), 8.04 (s, 1H), 8.80 (d, J=5.7 Hz, 2H). ES-MS: 314.3 (M+H)

Example 2o

Synthesis of 6-methyl-8-bromo-3-hydroxy-2-(4-pyridinyl)-4H-benzopyran-1-one

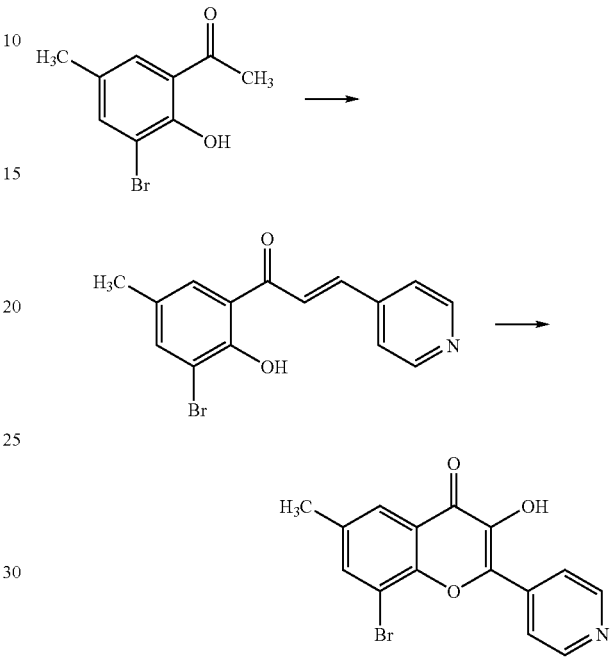

To a mixture of 3'-bromo-2'-hydroxy-5'-methylacetophenone (1.15 g) and pyridine-4-carboxaldehyde (0.54 g) in ethanol (10 ml) was added dropwise 50% sodium hydroxide solution and the mixture was stirred at room temperature for 4 h. The mixture was treated with ice cold glacial acetic acid to pH 5.5, and a precipitate formed, which was filtered yielding the chalcone intermediate as a yellow solid (0.85 g).

The chalcone (0.132 g) in methanol (2.3 ml) at 0° C. was treated with 2N sodium hydroxide (2.1 ml) followed by 30% (v/v) hydrogen peroxide solution (189 µL). The mixture was stirred overnight at 4° C. The mixture was neutralised with 2N sulfuric acid, and a precipitate formed which was filtered to yield a tan solid. ES-MS: 332.0, 334.0 (M+H)

Example 3

Preparation of Pyridine-Substituted Quinolone Derivatives

Pyridine-substituted quinolone compounds of the present invention were prepared according to the following general method:

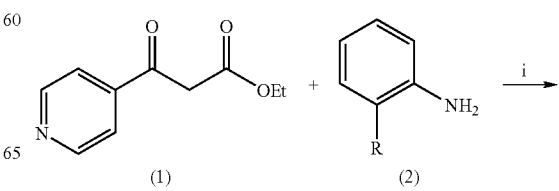

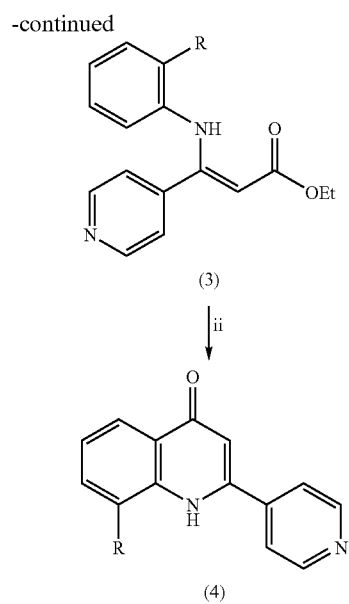

Reagents: i. p-toluenesulfonic acid, toluene, reflux; ii. Ph₂O, heat.

i. Synthesis of ester intermediate (compound 3): Ethyl β-oxo-4-pyridinepropanoate (compound 1, 4.35 mmol) [Lesher et al., 1984, *J. Heterocycl. Chem.* 21(6): 1849], aniline (compound 2, 3.35 mmol) and p-toluenesulfonic acid (0.54 mmol) in toluene (30 mL) were heated at reflux temperature for 18 hours, with azeotropic removal of water. Evaporation of the solvent under reduced pressure yielded a crude yellow oil which, after purification by flash chromatography, using petroleum ether/ethyl acetate (1:1) as eluent, afforded ester intermediate (compound 3, 70-80%).

ii. Synthesis of quinolone (compound 4): Ester intermediate (compound 3) (2.58 mmol) was refluxed in diphenyl ether (3 mL) for 20 minutes, cooled to room temperature and treated with petroleum ether to afford cream solid. The precipitate was filtered, washed several times with petroleum ether and purified by flash chromatography, using ethyl acetate/methanol (9:1) as eluent to afford the required quinolone compound 4 (60-70%).

8-phenoxy-2-(4-pyridinyl)-4-(1H)-quinolinone (KN-319)

Ester intermediate (compound 3, where R is OPh) cyclised in situ affording quinolone (compound 4) upon refluxing in toluene (step i): ¹H NMR (400 MHz, CDCl₃): δ 6.64 (d, J=1.9 Hz, 1H), 7.06 (dd, J=8.0, 1.1 Hz, 1H), 7.15 (dd, J=7.7, 0.7 Hz, 2H), 7.20-7.31 (m, 2H), 7.44 (td, J=7.7, 0.7 Hz, 2I), 7.57 (dd, J=5.0, 1.4 Hz, 2H), 8.06 (dd, J=8.0, 1.1 Hz, 1H), 8.80 (d, J=5.0 Hz, 2H), 8.88 (br.s, NH); MS-ES m/e 315 (M+H).

8-bromo-2-(4-pyridinyl)-4-(1H)-quinolinone (KN-343)

Ester intermediate (compound 3, where R is Br): ¹H NMR (300 MHz, CDCl₃) δ 1.33 (t, J=7.1 Hz, 3H), 4.25 (q, J=7.1 Hz, 2H), 5.17 (s, 1H), 6.31 (dd, J=7.7, 1.6 Hz, 1H), 6.81 (td, J=7.7, 1.6 Hz, 1H), 6.89 (td, J=7.7, 1.6 Hz, 1H), 7.21 (d, J=5.2 Hz, 2), 7.54 (dd, J=7.7, 1.6 Hz, 1H), 8.56 (d, J=5.2 Hz, 2H), 10.16 (br.s, NH); MS-ES m/e 347 (M+H).

Quinolone (compound 4): ¹H NMR (400 MHz, (CD₃)₂SO) δ 7.45 (t, J=7.9 Hz, 1H), 7.49 (s, 1H), 8.12 (d, J=5.2 Hz, 2H), 8.14 (dd, J=7.9, 1.3 Hz, 1H), 8.19 (dd, J=7.9, 1.4 Hz, 1H), 8.78 (d, J=5.2 Hz, 2H), 12.02 (br.s, NH); MS-ES m/e 301 (M+H).

KN-343 is an intermediate in the synthesis of various other pyridine-substituted quinolone analogues.

8-(4-Fluoro-2-methylphenoxy)-2-(4-pyridinyl)-4-(1H)-quinolinone (KN-337)

Ester intermediate (compound 3, where R is 4-fluoro-2-methylphenoxy): ¹H NMR (400 MHz, CDCl₃): δ 1.29 (t, J=7.1 Hz, 3H), 2.26 (s, 3H), 4.20 (q, J=7.1 Hz, 2H), 5.07 (s, 1H), 6.41 (dd, J=7.7, 1.9 Hz, 1H), 6.56 (dd, J=7.7, 1.9 Hz, 1H), 6.69 (td, J=7.7, 1.9 Hz, 1H), 7.76 (dd, J=8.9, 5.0 Hz, 1H), 6.81-6.86 (m, 2H), 6.97 (dd, J=8.9, 3.1 Hz, 1H), 7.27 (dd, J=4.5, 1.5 Hz, 2H), 8.57 (dd, J=4.5, 1.5 Hz, 2H), 10.25 (s, NH); MS-ES m/e 393 (M+H).

Quinolone (compound 4): ¹H NMR (400 MHz, CDCl₃): δ 2.23 (s, 3H), 6.67 (d, J=2.1 Hz, 1H), 6.76 (dd, J=8.1, 1.0 Hz, 1H), 6.98 (td, J=8.2, 2.8 Hz, 1H), 7.03-7.07 (m, 2H), 7.20 (t, J=8.1 Hz, 1H), 7.62 (dd, J=4.5, 1.6 Hz, 2H), 8.02 (dd, J=8.1, 1.0 Hz, 1H), 8.84 (dd, J=4.5, 1.6 Hz, 2H), 8.86 (s, NH); MS-ES m/e 347 (M+H).

8-methoxy-2-(4-pyridinyl)-4(1H)-quinolinone (KN-344)

Ester intermediate (compound 3, where R is OMe) cyclised in situ affording quinolone (compound 4) upon refluxing in toluene (step i): ¹H NMR (400 MHz, (CD₃)₂SO) δ 3.99 (s, 3H), 6.66 (s, 1H), 7.25 (dd, J=7.9, 1.3 Hz, 1H), 7.32 (t, J=7.9 Hz, 1H), 7.70 (dd, J=7.9, 1.3 Hz, 1H), 7.82 (dd, J=4.4, 1.7 Hz, 2H), 8.72 (dd, J=4.4, 1.7 Hz, 2H); MS-ES m/e 253 (M+H). KN-344 is a key intermediate in the synthesis of various other pyridine-substituted quinolone analogues.

8-phenyl-2-(4-pyridinyl)-4(1H)-quinoline (KN-345)

Ester intermediate (compound 3, where R is phenyl) cyclised in situ affording quinolone (compound 4) upon refluxing in toluene (step i): ¹H NMR (400 MHz, CDCl₃) δ 6.65 (d, J=2.0 Hz, 1H), 7.38 (dd, J=4.5, 1.7 Hz, 2H), 7.46 (td, J=8.1, 1.6 Hz, 1H), 7.52-7.56 (m, 3H), 7.58-7.63 (m, 2H), 8.42 (dd, J=8.1, 1.6 Hz, 2H), 8.75 (dd, J=4.5, 1.7 Hz, 2H); MS-ES m/e 299 (M+H).

8-Benzyl-2-(4-pyridinyl)-4(1H)-quinolinone (KN-346)

Ester intermediate (compound 3, where R is benzyl) cyclised in situ affording quinolone (compound 4) upon refluxing in toluene (step i): ¹H NMR (400 MHz, CDCl₃) δ 4.34 (s, 2H), 6.52 (s, 1H), 7.27-7.33 (m, 3H), 7.37-7.44 (m, 4H), 7.63 (d, J=6.9 Hz, 2H), 8.35 (d, J=8.3 Hz, 1H), 8.67 (br.s, 2H); MS-ES m/e 313 (M+H).

8-Nitro-2-(4-pyridinyl)-4(1H)-quinolinone (KN-352)

Ester intermediate (compound 3, where R is a nitro group) was used crude, without further purification in the synthesis of quinolone (compound 4): ¹H NMR (400 MHz, CDCl₃) δ 6.77 (d, J=2 Hz, 1H), 7.51 (t, J=7.9 Hz, 1H) 7.65 (dd, J=4.5, 1.7 Hz, 2H), 8.72 (dd, J=7.9, 1.6 Hz, 1H) 8.80 (ddd, J=7.9, 1.6, 0.6 Hz, 1H) 8.89 (dd, J=4.5, 1.7 Hz, 2H); MS-ES m/e 268 (M+H).

8-Amino-2-(4-pyridinyl)-4(1H)-quinolinone (KN-353)

8-Nitro-2-(4-pyridinyl)4(1H)-quinolinone (KN-352) was hydrogenated using Pd/C in ethanol to afford the title compound: MS-ES m/e 238 (M+H).

8-Naphthyl-2-(4-pyridinyl)-4(1H)-quinolinone (KN-350)

Ester intermediate (compound 3, where R is naphthoxy): $^1$H NMR (400 MHz, CDCl$_3$): δ 1.23 (t, J=7.1 Hz, 3H), 4.13 (q, J=7.1 Hz, 2H), 5.01 (d, J=1.6 Hz, 1H), 6.56 (dd, J=7.8, 1.6 Hz, 1H), 6.77-6.82 (m, 3H), 6.88 (td, J=7.8, 1.6 Hz, 1H), 7.27 (dd, J=4.5, 1.6 Hz, 2H), 7.37 (t, J=8.1 Hz, 1H), 7.50-7.54 (m, 2H), 7.62 (d, J=8.1 Hz, 1H), 7.85-7.89 (m, 1H), 8.18-8.21 (m, 1H), 8.57 (dd, J=4.5, 1.6 Hz, 2H), 10.24 (s, NH); MS-ES m/e 410 (M+H).

Quinolone (compound 4): $^1$H NMR (400 MHz, CDCl$_3$): δ 6.69 (d, J=2.1 Hz, 1H), 6.97 (dd, J=7.6, 1.2 Hz, 1H), 7.16 (dd, J=7.6, 1.2 Hz, 1H), 7.21 (t, J=8.1 Hz, 1H), 7.48 (t, J=7.9 Hz, 1H), 7.52-7.55 (m, 2H), 7.59 (td, J=7.6, 1.2 Hz, 1H), 7.78 (d, J=8.1 Hz, 1H), 7.96 (d, J=7.9 Hz, 1H), 8.07 (d, J=7.9 Hz, 1H), 8.08 (d, J=8.1 Hz, 1H), 8.79 (dd, J=4.5, 1.6 Hz, 2H), 8.94 (br.s, NM; MS-ES m/e 365 (M+H).

Example 4

Preparation of Pyridine-Substituted Pyridopyrimidinone Derivatives

Example 4a

General Experimental Procedure: A mixture of the amine (3.00 mmol) and ethyl γ-oxo-4-pyridinepropanoate (3.00 mmol) was heated at 180-200° C. for 20-45 min. The crude material was subsequently purified by column chromatography (SiO$_2$, EtOAc) to afford the required pyrimidine. The reaction yields were between 10-20%.

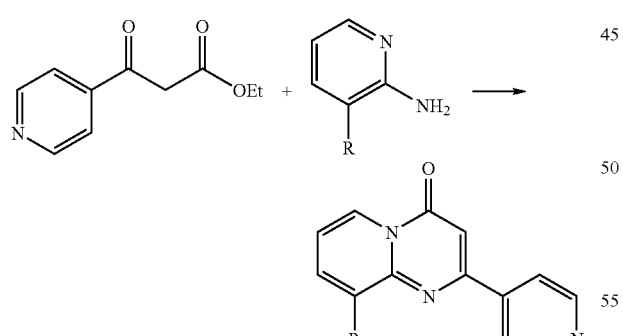

9-methyl-2-(4-pyridinyl)-4H-Pyrido[1,2-a]pyrimidin-4-one (KN-347)

$^1$H NMR (CDCl$_3$, 200 MHz) δ 2.75 (s, 3H); 7.03 (s, 1H); 7.15 (t, J=6.97 Hz, 1H), 7.69-7.73 (bd, J=6.91 Hz, 1H); 8.12-8.15 (bd, J=6.05 Hz, 2H); 8.82-8.84 (bd, J=4.73 Hz, 2H); 9.01-9.05 (bd, J=7.40 Hz, 1H). LCMS m/z 238 (M$^+$+H).

9-Benzyl-2-(4-pyridinyl)-4H-Pyrido[1,2-a]pyrimidin-4-one (KN-349)

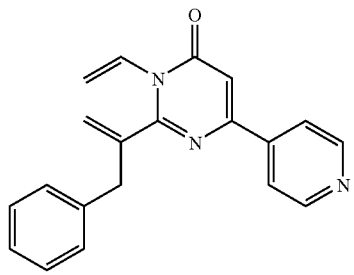

$^1$H NMR (CDCl$_3$, 300 MHz) δ 4.50 (s, 2H); 7.03 (s, 1H); 7.16 (t, J=7.03 Hz, 1H); 7.28-7.39 (m, 5H); 7.56-7.58 (m, 1H); 8.21 (s, 2H); 8.83 (s, 2H); 9.02-9.05 (m, 1H). LCMS m/z 314 (M$^+$+H).

9-Phenyl-2-(4-pyridinyl)-4H-Pyrido[1,2-a]pyrimidin-4-one (KN-348)

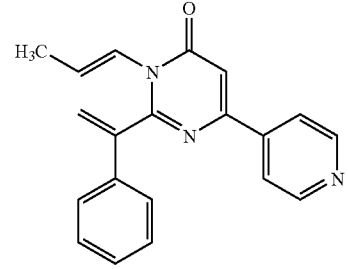

$^1$H NMR (CDCl$_3$, 300 MHz) δ 2.50 (d, J=1.07 Hz, 3H); 7.00 (s, 1H); 7.48-7.56 (m, 4H); 7.71-7.75 (n, 4H); 7.90 (bs, 2); 8.96 (m, 1H). LCMS m/z 314 (M$^+$+H).

9-Bromo-2-(4-pyridinyl)-4H-Pyrido[1,2-a]pyrimidin-4-one

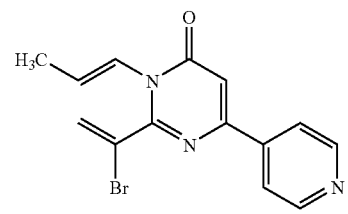

$^1$H NMR (DMSO, 300 MHz) δ 2.42 (m, 3H); 7.23 (s, 1H); 8.19 (dd, J=4.48, 1.66 Hz, 2H); 8.40 (d, J=1.95 Hz, 1H); 8.77 (dd, J=4.56, 1.65 Hz, 2H); 8.83 (m, 1H). LCMS m/z 316(M$^+$).

Example 4b 9-(2-phenethyl)amino-2-(4-pyridinyl)-4H-Pyrido[1,2-a]pyrimidin-4-one (KN-316)

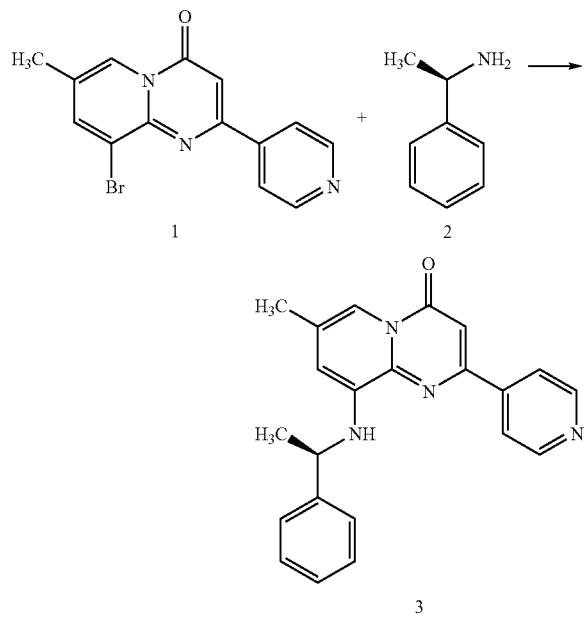

A mixture of a bromo derivative 1 (324 mg, 1 mmol), (R)-(+)-α-methylbenzylamine 2 (122 mg, 1 mmol), potassium t-butoxide (225 mg, 2 mmol) and PdCl₂ (dppf) (35 mg, 0.05 mmol) in THF was stirred at refluxing temperature for 20 hours over a nitrogen atmosphere. The reaction mixture was cooled and diluted with ethyl acetate. The organic layer was washed with water, brine and dried over Na₂SO₄. The ethyl acetate layers was concentrated in vacuo and the residue was subjected to column chromatography (silica gel, ethylacetate) to give the required product 3. ¹H NMR (300 MHz, CDCl₃), δ 8.78 (br s, 2H), 8.21 (s, 1H), 7.92 (d, J=5.9 Hz, 2H), 7.4-7.26 (m, 5H), 6.90 (s, 1H), 6.50 (d, J=5.5 Hz, 1H, —NH), 6.27 (s, 1H), 4.60 (m, 1H), 2.23 (s, 3H), 1.71 (d, J=6.9 Hz, 3H). MS (m/z)=357.13 (m+1).

Example 4c

Alternate synthesis of 9-Bromo-2-(4-pyridinyl)-4H-Pyrido[1,2-a]pyrimidin-4-one

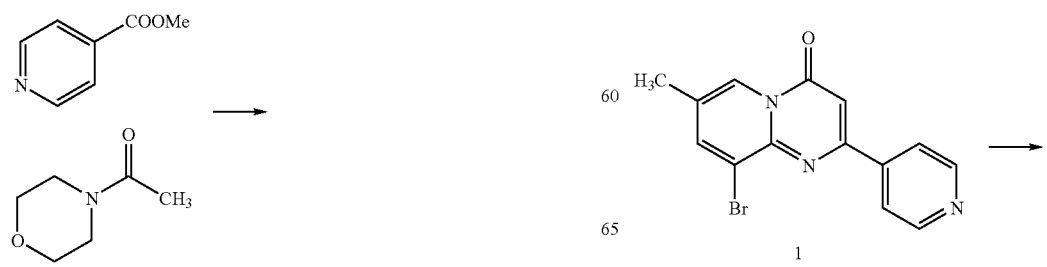

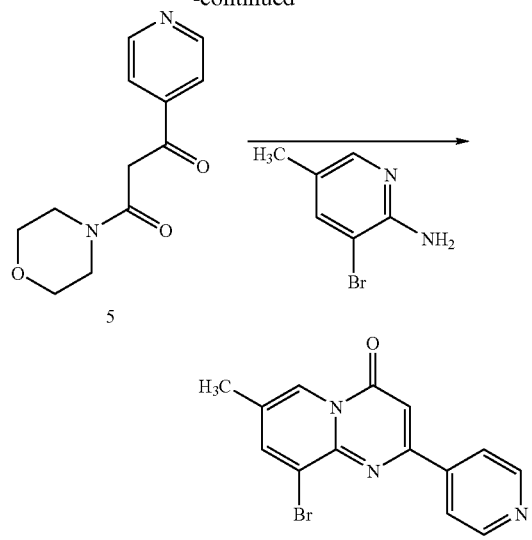

A solution of ethyl isonicotinate (5.0 ml, 25.91 mmol) and 4-acetylmorpholine (3.0 ml, 25.91 mmol) in THF (25 ml) was treated with a solution of lithium bis(trimethylsilyl)amide (7.0 g, 41.83 mmol) in THF (25 ml). The subsequent solution was stirred at ambient temperature for 24 h. The solution was filtered and washed with ether (3×50 ml). The filtrate was dissolved in water (100 ml), acidified with glacial acetic acid, extracted with CH₂Cl₂ (3×30 ml), dried (Na₂SO₄), filtered and evaporated to dryness. The crude reaction mixture was purified via column chromatography (SiO₂, ethyl acetate) to yield compound 5 as a yellow tinged viscous oil which solidified on standing (3.6 g, 59%). ¹H NMR (CDCl₃, 300 MHz) combined NMR of ketone and enol ether δ 3.47-3.57 (bm, 8H); 3.95 ans 5.77 (s, 1H); 7.44 and 7.61 (dd, J=4.43, 1.62 Hz, 2H); 8.49 (bd, J=5.93 Hz) and 8.64 (dd, J=4.44, 1.62 Hz) 2H. LCMS m/z 235 (M⁺+H).

A mixture of 2-amino-3-bromo-5-methylpryidine (1.00 g, 4.30 mmol), compound 5 (1.20 g, 6.40 mmol) and p-toluenesulfonic acid monohydrate (203.0 mg, 1.07 mmol) in toluene (50 ml) was refluxed for 4 days. The toluene was removed in vacuo and the resulting crude reaction mixture was purified via column chromatography (SiO₂, ethyl acetate) to give compound 5 as a yellow precipitate (0.66 g, 65%).

Example 4d

-continued

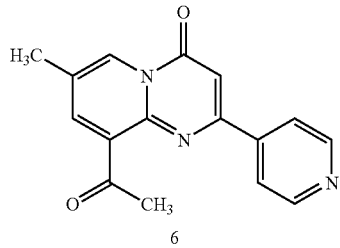

6

A solution of 9-Bromo-2-(4-pyridinyl)-4H-Pyrido[1,2-a]pyrimidin-4-one, 1 (232.1 mg, 0.73 mmol), butyl vinyl ether (0.19 ml, 1.08 mmol), potassium carbonate (149.2 g, 1.49 mmol) and Pd(OAc)2 (4.8 mg, 21.6 µmol) in dry DMF (6 ml) was stirred under an atmosphere of nitrogen at 90-100° C. for 2 h. The solution was treated with 1M HCl until the mixture was rendered acidic (~pH 4) and the subsequent solution was stirred for 3 h at ambient temperature. The reaction was diluted with water (10 ml), neutralised with NaHCO$_3$ and the aqueous layer was extracted with CH$_2$Cl$_2$ (3×15 ml). The combined organic extracts were washed with water (3×15 ml), dried (Na$_2$SO$_4$), filtered and concentrated to dryness to give a brown coloured precipitate. The solid was triturated with ether, filtered, washed with additional ether (3×15 ml) and air dried to give the desired ketone 6 as a yellow precipitate (61.4 mg, 30%). $^1$H NMR (CDCl$_3$, 300 MHz) δ 2.50 (d, J=3.29 Hz, 3H); 2.93 (s, 3H); 7.03 (s, 1H); 8.03 (d, J=2.18 Hz, 1H); 8.16 (bd, J=6.37 Hz, 2H); 8.83 (bs, 2H); 9.03 (m, 1H). LCMS m/z 280 (M$^+$+H).

BIOLOGICAL EXAMPLES

Example 1

PI 3-kinase β Selectivity

The ability of TGX-221 to selectively inhibit the activity of the Type I PI 3-kinase β over other Type I PI 3-kinase family members, or other related kinase family enzymes, was examined using an in vitro enzyme assay.

To examine the inhibitory activity of TGX-221 against PI 3-kinase α, β or δ isoforms, or PI4 kinase, washed platelets were lysed with 1× lysis buffer (10 mM Tris, pH 7.6, 10 mM PMSF, 5 mM EDTA, 2 mM benzamidine, 0.1% Triton X-100) and whole cell lysates were clarified by centrifugation at 15,000×g for 5 minutes. For each immunoprecipitation, 1 mg of lysate was incubated with an anti-p110α (1 µg), anti-p110β (1 µg), anti-p110δ (1 µg) or anti-PI4 kinase antibody (2-5 µg) and 50 µl of a 50% slurry of protein A beads overnight at 4° C. For PI 3-kinase assays, the protein A beads-immune complexes were washed twice with lysis buffer and twice more with 1× PI 3-kinase assay buffer (20 mM Hepes, pH 7.2, 5 mM MgCl$_2$, 0.25 mM EDTA) prior to incubating 25 µl of the immunoprecipitated p110 α or β isoforms with 40 µl of the PI 3-kinase substrate, phosphatidylinositol (PtdIns), 10 µl ATP mix (0.5 µl γ$^{32}$ P-ATP+0.5 µl 10 nM ATP), 10 µl 10× kinase buffer, 15 µl milliQ H$_2$O and 1 µl of TGX-221 (0-10 µM) for 60 minutes at room temperature. For PI4 kinase assays, protein A beads-immune complexes were also washed twice with lysis buffer, prior to two washes with 1× PI4 kinase assay buffer (20 mM Hepes, pH 7.5, 10 mM MgCl$_2$, 0.3% Triton X-100) and the addition of other assay constituents, as described above. All reactions were terminated by the addition of 100 µl 1 M HCl, 200 µl choloroform/methanol (1:1) and 500 µl 2 M KCl and lipids extracted by centrifugation at 15,000×g for 2 minutes. The production of PI3 or PI4 kinase lipid products, PtdIns(3)P and PtdIns(4)P, were confirmed through TLC analysis. The lipid spots were then removed from the TLC plate and the level of radioactivity quantified to accurately determine the level of PtdIns(3)P/PtdIns(4)P production.

To examine the ability of TGX-221 to inhibit the PI 3-kinase γ isoform, 0.5 µg p110γ recombinant protein was incubated with 10 µl 10× kinase buffer (2.5 mM EDTA, 200 mM HBEPES, 50 mM MgCl$_2$ pH 7.2), 30 µl milliQ H$_2$O, 40 µl PI (150 µg/ml), 10 µl ATP mix (0.5 µl γ$^{32}$ P-ATP+0.5 µl 10 mM ATP) and 1 µl of TGX-221 (0-10 µM) for 20 minutes at room temperature. Reactions were terminated and lipid products analysed as described above for the other PI 3-kinase isoforms assays.

The inhibitory activity of TGX-221 against other tyrosine and Ser/Thr kinases were performed by MDS Pharma Services (Panlabs, Taiwan).

TGX 221 showed an IC$_{50}$ of 5 nM against PI 3-kinase β and exhibited >100-fold selectivity against the two other major type I PI 3-kinase isoforms in platelets (PI 3-kinase α and PI 3-kinase γ).

| E. Enzyme | TGX-221 IC$_{50}$ (µM) |
|---|---|
| Lipid Kinases | |
| p110α-PI3K | 5 |
| p110β-PI3K | 0.005 |
| p110γ-PI3K | >10 |
| p110δ-PI3K | 0.1 |
| PI4K | >10 |
| Tyrosine Kinases | |
| Abl | >10 |
| EGF Receptor | >10 |
| Fyn | >10 |
| HER2 Receptor | >10 |
| Insulin Receptor | >10 |
| Ser/Thr Kinases | |
| Casein Kinase 2 | >10 |
| Cdk2/cyclin A | >10 |
| ERK1 | >10 |
| p38α | >10 |
| p70$^{S6}$ | >10 |
| PKA Non-selective | >10 |
| PKC Non-selective | >10 |
| CaMK | >10 |

TGX-221 demonstrated >1000 fold selectivity for PI 3-kinase β over a broad range of protein kinases. This result is shown in FIG. 2D. TGX-221 showed a minimal inhibitory effect on PI4 kinase (FIG. 2D) and selectively inhibited PI 3-kinase lipid generation in vivo FIG. 3A), without altering the cellular levels of the conventional phosphoinositides, PtdIns, PtdIns(4)P (data not shown) and PtdIns(4,5)P$_2$ (FIG. 3A).

The inhibitory concentration for each of the tested compounds is listed in the following Table.

TABLE I

Activity of selected compounds against isoforms of PI 3-kinase

| TGX# | Substitution Pattern | alpha | beta | gamma | delta | Ratio δ/β |
|------|---------------------|-------|------|-------|-------|-----------|
|      |                     |       |      | nM    |       |           |
| 195  | 7-methyl-9-{[methyl(phenyl)amino]methyl} | >5000 | 20 | >5000 | 500 | 25.00 |
| 221  | 7-methyl-9-(1-phenylaminoethyl) | >5000 | 5 | >5000 | 100 | 20.00 |
| 239  | 9-[1-(3,5-difluorophenylamino)ethyl]-7-methyl | >5000 | 7 | >5000 | 80 | 11.43 |
| 243  | 9-[1-(4-chlorophenylamino)ethyl]-7-methyl | >5000 | 50 | >5000 | 2000 | 40.00 |
| 244  | 9-[1-(3,4-dichlorophenylamino)ethyl]-7-methyl | >5000 | 50 | >5000 | 1000 | 20.00 |
| 248  | 9-[1-(3-chlorophenylamino)ethyl]-7-methyl | >5000 | 10 | >5000 | 100 | 10.00 |
| 262  | 7-methyl-9-[1-(3-methylphenylamino)ethyl] | >5000 | 50 | >5000 | 1000 | 20.00 |
| 264  | 7-methyl-9-[1-(3-trifluoromethylphenylamino)ethyl] | >5000 | 75 | >5000 | 10000 | 133.33 |
| 295  | 7-methyl-9-[1-(2-pyridinylamino)ethyl] | >5000 | 50 | >5000 | 2000 | 40.00 |

Example 2

Shear-Induced Platelet Aggregation Studies

The ability of TGX-221 to inhibit the production of PI 3-kinase lipid products and platelet aggregation induced by pathological levels of shear was examined using a custom-made cone & plate device.

For this assay, whole blood was collected in the presence of anti-coagulant [6 volumes blood to 1 volume anticoagulant (90 mM sodium citrate, 7 mM citric acid, pH 4.6, 140 mM dextrose and 70 mM theophylline)] and platelets isolated and washed using a modified method of Baezinger and Majerus (1974). Briefly, platelet-rich plasma (PRP) was obtained by centrifugation of whole blood at 200×g for 30 minutes. Platelets were then pelleted by centrifugation of the PRP at 2,000×g for 10 minutes. The platelet pellet was resuspended in platelet washing buffer (PWB) [4.3 mM $K_2HPO_4$, 4.3 mM $Na_2HPO_4$, 24.3 mM $NaH_2PO_4$, pH 6.5, 113 mM NaCl, 5.5 mM glucose, 0.5% bovine serum albumin (BSA) and 10 mM theophylline]. Platelets were then washed twice with phosphate-free Tyrode's buffer containing the platelet activation inhibitor, theophylline (10 mM), prior to being labeled with 0.3 mCi/ml inorganic $^{32}P$ for 2 hours at 37° C. Unincorporated $^{32}P$ was removed by washing platelets twice with phosphate-free Tyrode's buffer in the presence of theophylline (10 mM) prior to resuspending platelets in Theophylline-free Tyrode's buffer containing 1 mM calcium. Radioactively labeled platelets were incubated with increasing concentrations of TGX-221 (0-500 nM) for 30 min at 37° C. vWf (10 μg/ml) was added immediately prior to subjecting platelets to a pathological shear rate of 5000 $s^{-1}$ for a period of 2 min. Platelets were then lysed, extracted and separated by HPLC analysis according to Stephens et al. (1997, Cell, 89:105-114). Lipid peaks co-eluting with commercially available $PtdIns(3,4)P_2$ and $PtdIns(4,5)P_2$ standards were integrated and normalized to total lipid applied and expressed as a fraction of control samples.

To examine the effect of TGX-221 on platelet aggregation induced by pathological shear rates, washed platelets suspended in Tyrode's buffer containing 1 mM calcium (350×$10^9$) were incubated with increasing concentrations of TGX-221 (0-1 μM) for 10 min at 37° C. vWf (10 μg/ml) was added immediately prior to subjecting platelets to a pathological shear rate of 5000 $s^{-1}$ for a period of 5 min. Platelet samples were aspirated and the level of platelet aggregation determined by analyzing the number of unincorporated single platelets using a Sysmex™ KN-21N hematology analyzer. All data were normalized to control experiments and expressed as the proportional increase relative to control samples. TGX-221 effectively inhibited shear induced platelet aggregation over a concentration range ($IC_{50}$=0.05-0.1 μM) comparable to the inhibition of 3-phosphorylated lipids (FIG. 3B).

Example 3

FACS Analysis

The effect of TGX-221 on integrin activation and platelet activation was determined using FACS analysis. Washed platelets suspended in Tyrode's buffer containing 1 mM $CaCl_2$/1 mM $MgCl_2$ were incubated with 1 μg/ml anti-P selectin or 1 μg/ml PAC-1 antibody and vehicle alone or 0.5 μM TGX-221 for 10 min at 37° C. Platelets were then stimulated with thrombin (1 U/ml), ADP (12.5 mM), U46619 (1 μM) or collagen (10 μg/ml) for 20 min at room temperature prior to being fixed with 2% paraformaldehyde for 45 min at room temperature. Fixed platelets were washed twice with Tyrode's buffer, incubated with 1 μg/ml FITC-conjugated anti-mouse F(ab)$_2$' antibody for 15 min at room temperature, washed twice with Tyrode's buffer, resuspended to a final volume of 500 μl in Tyrode's buffer and analyzed by FACS.

Example 4

In Vitro Flow Studies

The effect of TGX-221 on platelet calcium flux was examined using a flow-based adhesion assay. Washed platelets (1.5×$10^9$) suspended in PWB were incubated with the calcium indicator dyes, Oregon Green 488 BAPTA-1, AM (1 μM) and Fura Red, AM (1.25 μM), for 30 min at 37° C. Platelets were washed twice with PWB prior to being resuspended in Tyrode's buffer containing 1 mM calcium. Platelets were incubated with vehicle alone, TGX-221 (0.5 μM), LY294002 (20 μM), aspirin (1 mM), apyrase (0.5 U/ml) or Aggrastat (200 nM) for 10 min prior to the performance of static or flow-based adhesion assays.

For static adhesion assays, platelets were allowed to settle on the surface of vWf-coated coverslips for 30 min at 37° C. For flow assays, platelets were either perfused over a vWf-coated microcapillary tube at a constant shear rate of 600, 1800 or 10,000 $s^{-1}$ or allowed to settle on the surface of a vWf-coated microcapillary tube prior to being accelerated through a shear gradient of 10,000 $s^{-1}$ over a 1 s interval. Real time platelet calcium flux in individual platelets was monitored at 1 s intervals over the 30 min incubation period or at 0.586 s intervals for up to 175 s for static and flow-based assays, respectively.

Example 5

Assay in Modified Folts Model

In vivo antithrombotic activity of TGX-221 was investigated using a modified folts model in anaesthetised rats and rabbits. Studies were approved by the University of Melbourne Animal Ethics Committee in accordance with the guidelines of the National Health & Medical Research Council of Australia. Anaesthesia was induced in Sprague-Dawley rats (260-400 g) with sodium pentobarbitone (Nembutal; 60 mg/kg i.p.; Merial Australia Pty. Ltd., Sydney, NSW, Australia), and in New Zealand White rabbits (2-3 kg) with pentobarbitone (15 mg/kg i.v.) and fentanyl (6 µg/kg i.v.; David Bull Laboratories, Mulgrave, VIC, Australia). Animals were mechanically ventilated (Ugo Basile ventilator, Comerio, VA, Italy) with room air supplemented with $O_2$. Body temperature was maintained throughout the experiment. Arterial blood pressure was measured via a femoral artery catheter connected to a pressure transducer (Model 1050.1, AD Instruments, Sydney, NSW) and a blood flow probe (1 mm i.d. for rats & 2.5 mm i.d. for rabbits; flowmeter T206, Transonic Systems Inc., Ithaca, N.Y., USA) was placed around each (control and test) carotid artery; all parameters were recorded on a PowerLab data acquisition system (8SP; AD Instruments). A silk suture was tied loosely around 1 artery, distal to the flow probe, for subsequent stenosis. Clexane (0.24 mg/kg rats & 1 mg/kg rabbits; enoxaparin sodium; Aventis Australia Pty. Ltd., Sydney, NSW, Australia) was administered i.v. 5 min prior to the experiment. The suture was tightened to cause a stenosis that decreased carotid blood flow by 50%. The segment of artery under the stenosis was then deendothelialised by pinching the artey over the suture 5 times with a pair of forceps. Carotid blood flow was monitored until it reached 0 ml/min, indicating a clot had formed at the site of stenosis. After 1 min, the site of stenosis was gently flicked, embolising the clot and restoring blood flow. Again, carotid blood flow was monitored until it reached 0 ml/min, and the time recorded. These cyclic flow reductions (CFRs) were observed for 30 min prior to drug administration. After 30 min, 0.25 ml/kg of propylene glycole as vehicle or 2 mg/kg of TGX-221 was administered as an i.v. bolus and blood flow was continuously measured for an additional 90 min. During this period, if CFRs were not abolished, or returned after a period of abolition, the clot was physically embolised (by flicking the vessel) each time blood flow reached zero, to restore CFRs. TGX-221 immediately abolished occlusive thrombus formation in 100% of rats (n=8) and rabbits (n=9) (FIG. 5A).

Example 6

Assay in Electrolytic Model

Distal to the left carotid artery flow probe, a piece of Parafilm was inserted under the vessel for electrical isolation. The artery was placed onto a hook-shaped platinum electrode, after which, it was clamped distally to the electrode to occlude blood flow and a current of 7 mA was delivered for 4 min using a constant current unit (Model CCU1, Grass Instruments, Quincy, Mass., USA) connected to a Grass SD9 stimulator. The artery clamp was released immediately after this 4 min period. Blood flow was monitored for 60 min after the end of the stimulation. Thrombosis formation was defined by blood flow falling to zero. In the test using the rat electrolytic injury carotid model (Bush & Shebuski, 1990), injection of TGX-221 (2 mg/kg in PG) 5 minutes before induction of injury completely prevented occlusive thrombus formation (n=6), compared with a 90% occlusion rate in vehicle-treated rats (n=10) (FIG. 5B), and preserved carotid blood flow volume over the 60 min post-injury period (FIG. 5B insert). TGX-221 had no effect on baseline arterial blood pressure, heart rate or blood flow in the uninjured carotid artery in both the Folts and electrolytic studies.

Example 7

Tail Bleeding Studies in Rats

Rats were anaesthetised with halothane in room air supplemented with $O_2$. Tail bleeding time was measured 15 min before drug administration (−15), and 5 and 30 min after administration. For experiments involving pretreatment with aspirin and clopidogrel, tail bleeding time was also measured before the first gavage dose at −25 h. Incisions 5 mm long and 1 mm deep were made in the tail at each time point and bleeding was monitored every 30 sec until it had ceased (=tail bleeding time).

Studies in rats as shown in FIG. 5C indicated that TGX-221 did not increase bleeding time when administered at >20 fold the minimum therapeutic concentration. Significantly, when TGX-221 (20 mg/kg i.v.) was administered alone or with heparin (100 U/kg i.v.), rat tail bleeding time was unaffected (FIG. 5C). In combination with clopidogrel (10 mg/kg p.o.)+heparin (100 U/kg i.v.), or aspirin (200 mg/kg p.o.)+heparin (100 U/kg i.v.), TGX-221 (2 mg/kg i.v.) did not exacerbate the prolonged bleeding time caused by these agents (FIG. 5C). TGX-221 (2 mg/kg i.v.) also did not affect bleeding time when administered in combination with either clopidogrel or aspirin.

Example 8

In Vitro PI 3-Kinase Assay

The effect of pyridine-substituted compounds on PI 3-kinase activity was determined using an in vitro PI 3-kinase assay. This assay was performed using PI 3-kinase immunoprecipitated from human platelets as the enzyme and PI as the substrate. The PI 3-kinase activity was quantitated by measuring the enzymatic incorporation of [$^{32}$P] into PI, forming PI([$^{32}$P]-3)P, as previously described (Susa et al., 1992, The Journal of Biological Chemistry 267(32):22951-22956.

Washed human platelets were lysed in Triton X-100 lysis buffer (10 mM Tris, pH 7.4, 1% Triton X-100, 2 mM EDTA, 1 mM PMSF) for 30 minutes. The Triton X-100 insoluble fraction was removed by centrifugation of the cell lysates at 15,000 g for 10 minutes. PI 3-kinase was immunoprecipitated by mixing 500 µg of the cell lysate with 1 µg of a rabbit anti-rat antibody against the p85/110 form of PI 3-kinase and 30 µl of 50% Protein A-sepharose beads for 2 hours at 4° C. The Protein A-sepharose-bound PI 3-kinase was isolated by pelleting the beads at 15,000 g for 5 seconds, and washing three times with ice-cold Triton X-100 lysis buffer followed by four washes with PI 3-kinase assay buffer (20 mM HEPES, pH 7.4, 1 mM EGTA, 5 mM $MgCl_2$).

PI stored in $CHCl_3$ was dried under $N_2$, resuspended in the lipid buffer (50 mM HEPES, pH 7.2, 1 mM EDTA) at a final concentration of 330 µg/ml, and sonicated for 6 minutes on ice. PI([$^{32}$P]-3)P was generated by mixing the immunoprecipitated PI 3-kinase for 20 minutes with 40 µl of the PI, 10 µl of ATP (1 mM) and $^{32}$P-r-ATP (0.5 µCi, 1 µCi/nmol), 10 µl of 10× kinase buffer, in a final assay volume of 100 µl adjusted with $H_2O$. TGX- was preincubated with the PI 3-kinase for 5 minutes prior to the addition of ATP. The assay was terminated with 100 µl of 1 N HCl, and the PI([$^{32}$P]-3)P product extracted with 200 µl chloroform:methanol (1:1) and 500 µl 2 M KCl. The PI([$^{32}$P]-3)P in the chloroform phase was resolved by thin layer chromatography using a solvent system containing $CHCl_3$:MeOH:HAC:$H_2O$ (43:38:5:7) (v:v:v:v), and visualized by autoradiography. The PI([$^{32}$P]-3)P spots were then scraped off from the TLC plates, deacylated with 1 ml methylamine:butanol:methanol (42:9:47) (v:v:v) for 4 hours at 53° C., and quantitated using a liquid scintillation counter (LKB 1209 RackBETA).

Example 9

Flow-Based Reconstitution Assay

The effect of TGX-286 on platelet adhesion was examined using a flow-based adhesion assay. Washed platelets were pretreated with 10, 25, or 50 nM TGX-286, or control buffer (0.1% DMSO) for 30 minutes at 37° C. prior to reconstitution with red blood cells to a hematocrit of 50%. The platelets and reconstituted red blood cells were perfused through vWf-coated glass microslides for 1 minute at a shear rate of 1800 $s^{-1}$. Non-adherent cells were removed by washing for 10 minutes at 1800 $s^{-1}$ and the number of adherent platelet were quantitated and expressed as the mean±SEM. TGX-286 inhibited the ability of platelets to adhere in a dose-dependent manner, showing a decrease of 51, 67 and 86% in platelet adhesion when platelets were pretreated with 10, 25, and 50 nM TGX-286.

Example 10

CD9-Antibody Induced Platelet Aggregation of Platelet Rich Plasma

The inhibitory effect of TGX286 and KN327 on platelet aggregation induced by the antibody CD9 was examined in platelet rich plasma (PRP). A suspension of PRP was incubated with 20-100 nM TGX286 or control buffer (0.1% DMSO) and treated with an aliquot of the antibody. Aggregation under stirring was monitored in a four channel aggregometer for 10 minutes. The level of aggregation was measured as the change in light transmission through the sample cell. The IC50 concentration is derived as the concentration of test compound at which aggregation of the PRP is inhibited by 50%.

Whole-Blood Flow Assay

The inhibitory effect of TGX-286 on platelet thrombus formation was examined using a whole-blood flow assay, since thrombi formed by washed platelets are small and poorly reproducible. Anticoagulated whole blood was incubated with 50, 100, or 200 nM TGX-286, or control buffer (0.1% DMSO) for 30 minutes with gentle rocking prior to perfusion through vWf-coated glass microslides for 2 minutes at a shear rate of 1800 $s^{-1}$. Non-adherent platelets were removed by washing for 10 minutes at 1800 $s^{-1}$, and adherent erythrocytes were lysed with 1% ammonium oxalate. The level of thrombus formation was quantitated indirectly by measuring platelet LDH (U/L) levels in the whole cell lysates by spectrophotometry. Following a 2-minute perfusion of whole blood, platelet-rich thrombi were observed over the surface of the microslide. Pretreatment with TGX-286 inhibited the ability of platelet thrombi to form on the vWf matrix in a dose-dependent manner. Pretreatment of whole blood with 50, 100, and 200 nM TGX-286 led to a decrease of 25, 53, and 80% in thrombus formation relative to control.

Example 11

Animal Model of Internal Carotid Artery Occlusion

The inhibitory effect of TGX-286 was examined in the well established animal model of arterial thrombosis of Folts et al., 1982, Circulation 65:248-255. This model is used to investigate the effects of antithrombotic drugs on clotting time in vivo in response to a crash injury followed by arterial stenosis.

The carotid artery of an anesthetized rat is dissected out, and an electromagnetic flow probe is placed around the artery to measure blood flow. Proximal to the flow probe, the artery is clamped with surgical forceps covered with silicone tubing to cause intimal and medial damage to the vessel wall. A ligature, or plastic cylinder of appropriate inside diameter is laced around the artery to produce a 70% reduction in arterial diameter.

Platelets aggregate in the area of the stenosed and damaged arterial vessel, gradually forming an occlusive platelet thrombus, seen as a decrease in blood flow. As the thrombus forms, blood pressure increases, causing the thrombus to fragment and embolize distal to the stenosed site. If the thrombus does not embolize spontaneously, the stenosed region is shaken gently to dislodge the thrombus. This causes a sudden restoration of blood flow. Platelets again aggregate in the area of the stenosed and damaged arterial vessel, repeating the thrombus-embolization pattern. This acute, platelet-mediated thrombus formation, followed by embolization, causes Cyclic Flow Reductions (CFR) in blood flow. Once a rat produces regular CFRs, an anti-thrombotic compound or vehicle control is administered via the jugular vein.

TGX-286 or KN327 were administered at doses of 2.5 mg/kg and 4 mg/kg via the jugular vein and the stabilization of blood flow was recorded. TGX-286, and KN327 at 14.0 mg/kg, returned 80% of the treated animals to baseline within 10 minutes, indicating that the compounds have utility in the treatment of coronary artery occlusion.

Example 12

Effect of TGX-286 and KN-327 on Platelet Thrombus Formation Under Flow

Citrated whole blood was pretreated with 50, 100 or 200 nM TGX-286, KN-327, or control buffer (0.1% DMSO) for 10 minutes at 37° C. Blood was perfused through von Willebrand factor—(vWf) coated microcapillary tubes for 2 minutes at 600 $s^{-1}$. Non-adherent cells were removed by perfusion of buffer for 2 minutes at 600 $s^{-1}$ and any adherent erythrocytes lysed through treatment with 1% ammonium oxalate. Adherent platelets were then lysed through addition of 1% Triton X-100 and lactate dehydrogenase (LDH) levels (U/L) analysed by spectrophotometry. Pretreatment of whole blood with 50, 100, 200 nM TGX-286 led to a decrease in thrombosis formation relative to control.

Example 13

Isoform Selective In Vitro PI3K Enzyme Assays

In vitro enzyme assays were conducted as a primary screen to determine drug candidate isoform affinity and specificity. The α and β isoforms of the PI3K were immunoprecipitated from a platelet lysate, using an antibodies obtained from Santa Cruz Biotechnology, that recognized specific regions of p110α (sc-7174) and β (sc-603) isoforms. The γ isoform was produced as a recombinant protein in the Kinacia laboratories. The δ isoform was immunoprecipitated from THP-1 cells in a similar manner using a δ isoform specific antibody (sc-7176). Standard phosphorylation assays using phosphatidylinositol and $^{32}P$ were used to measure the enzyme activity in the immunoprecipates in the presence or absence of an inhibitor. Enzyme activity was determined over a range of inhibitor concentrations to establish an $IC_{50}$ value.

The $IC_{50}$ for the PI3 kinase inhibitor, LY294002 (8-phenyl-2-(4-morpholinyl)-4H-benzopyran-4-one, Sigma #L9908) against the various isoforms of PI3K was in agreement with previously reported values (0.5-1.5 µM).

Example 14

Neutrophil ROS Response

Preparation of Leukocytes from Human Blood 3 ml of preservative free whole blood was placed in a 50 ml conical tube. 48 ml of erythrocyte lysing solution and gently mixed by inversion for 10 min at 25° C. on a haematology nutator and subsequently centrifuged for 10 min at 350×g at 25° C. in a table top centrifuge. The Leukocyte rich pellet was resuspended in phosphate buffered saline supplemented with 10% w/v gelatin (PBS-gel) and centrifuged as above. The Leukocyte pellet was washed once with Hanks' balanced salt solution (HBSS) and resuspended at a final cell count of $2 \times 10^6$/ml and used immediately.

Measurement of ROS Production from Neutrophils

Reactive Oxygen Species (ROS) generation is one of the hall-marks of neutrophil activation. A number of chemokines and cytokines potentiate ROS generation by neutrophils. The effect of the PI3K inhibitor TGX-286 on ROS generation following stimulation with the chemotactic peptide fmlp was measured. ROS generation was measured by monitoring the oxidation of intracellular dihydrorhodamine 123 (DHR) via fluorescence activated cell sorting (FACS) by modification of the method of Robinson et al., (pp 9.7.5-9.7.9 in Curr. Protocols in Cytometry (1997)). A Leukocyte suspension was bulk loaded with 2 µl of 50 mM DHR per ml cells (50 mM final) and incubated at 37° C. for 12 min. 500 µl aliquots of DHR loaded cells were stimulated with 5 µl of 100 µM fmlp working solution for 20 min at 37° C. and subsequently quenched on ice. The flow cytometer was set up with excitation at 488 nm using a 520±20 nm bandpass filter for DHR emission. An unstimulated control sample was utilized to identify and gate the neutrophil population and verified via anti-CD14 immunostaining. Fluorescence base-line data was calibrated using these gated control neutrophils. Stimulated cell samples were analysed and linear green fluorescence (DHR) was monitored for 5000 gated neutrophils from each sample. To measure the relative amounts of ROS values obtained from the control samples were subtracted from all and normalized to the values obtained from the fmlp alone samples (no inhibitor).

Example 15

Neutrophil Elastase Release

Preparation of Neutrophils from Human Blood

Aliquots (24 ml) of heparinised blood from healthy volunteers were layered on 12 ml cushions of Histopaque-119® and Histopaque-1077® (Sigma) and centrifuged at 700×g for 30 min at 25° C. in a table top centrifuge. The neutrophil rich band just above the Histopaque-119 cushion was collected and washed with HBSS. Residual erythrocytes were removed by hypotonic lysis with 0.2% NaCl. The neutrophil preparation was washed twice with HBSS and used immediately.

Measurement of Neutrophil Elastase Exocytosis

Activated Neutrophils respond to a range of stimuli by releasing several proteases that are responsible for the destruction of tissues and extra-cellular matrices during inflammation. As an indication of protease release, the effect of TGX-286 on neutrophil elastase exocytosis was measured. Elastase exocytosis was quantitated by modification of the procedure of Ciesla et al., (The Journal of Trauma, 48(3): 388-395 (2000)), as follows. Neutrophil elastase release was measured by cleavage of the specific elastase substrate AAPV-pNA. Isolated neutrophils ($6.25 \times 10^5$ cells) were pre-incubated at 37° C. for 5 min before stimulation with 0.1 µM fmlp for 20 min. The cell suspension was subsequently centrifuged at 400×g for 5 minutes, and the resulting supernatant aspirated and retained. Elastase release was assessed by addition of 100 µl of cell free supernatant to individual wells in a 96-well microplate containing 0.33 mM of the specific elastase chromogenic substrate AAPV-pNA in 33.3 mM hydroxyethylenepiperazine ethanesulfonic acid and 0.17 mM NaCl. Blank wells also contained the elastase inhibitor AAPV-CK (0.17 mM. Total reaction volume was 150 µL and each experiment was performed in duplicate with separate AAPV-CK blanks. The 96 well plate was incubated for 60 minutes at 37° C. and absorbance measured at 405 nm. To measure the relative amounts of elastase, values obtained from the control samples were subtracted from all and normalized to the values obtained from the fmlp alone samples (no inhibitor).

Example 16

Cell Proliferation Assay

The anti-proliferative activity of TGX-286 was determined U937 (monocytic) cell lines. The cytotoxic activity of the compounds was monitored over four days by counting cell number, and determining cell viability using a colorimetric assay of metabolic activity.

The inhibitory concentration (nM) for the tested compounds in each biological activity is listed in Table II below.

TABLE II

| Method # | Isolated enzyme assays(nM) IC50s | | |
|---|---|---|---|
| | Example 8 | Example 13 | |
| | Platelet IP (p85) | P110 γ | P110 δ |
| TGX258 | 10000 | >20000 | >10000 |
| TGX286 | 2 | 1000 | 100 |
| KN303 | 10 | 1500 | 500 |
| KN310 | 100 | 7500 | 1000 |
| KN312 | 50 | 10000 | 10000 |
| KN313 | 100 | 10000 | 5000 |
| KN315 | >100 | 5000 | 5000 |
| KN316 | 1000 | 20000 | 1000 |
| KN317 | >100 | 20000 | 5000 |
| KN319 | 500 | 20000 | 300 |
| KN322 | 1000 | 10000 | 1000 |
| KN326 | 500 | 5000 | 1000 |
| KN327 | 20 | 15000 | 500 |
| KN328 | 50 | 10000 | 10000 |
| KN333 | 10000 | >10000 | |
| KN335 | 1000 | 10000 | 1000 |
| KN336 | 1000 | 10000 | 200 |

TABLE II-continued

| | Isolated enzyme assays(nM) IC50s | | |
|---|---|---|---|
| Method | Example 8 | Example 13 | |
| # | Platelet IP (p85) | P110 γ | P110 δ |
| KN337 | 200 | >10000 | 200 |
| KN340 | 10000 | >10000 | >10000 |
| KN341 | 500 | 5000 | 50 |
| KN342 | 10000 | >10000 | >10000 |
| KN344 | 5000 | >10000 | |
| KN345 | 5000 | >10000 | 10000 |
| KN346 | >10000 | >10000 | 10000 |
| KN347 | >10000 | >10000 | >10000 |
| KN348 | >10000 | >10000 | >10000 |
| KN349 | 500 | >10000 | 2000 |
| KN350 | 500 | | |
| KN351 | 500 | | |

TABLE III

| Method # | P110α isoform Example 13 IC50/(nM) | P110 β isoform Example 13 IC50/(nM) | Platelet aggregation v. CD9 antibody Example 10 IC50/(nM) | Inhibition of Thrombus formation Example 12 IC50/(nM) | ROS release from neutrophils Example 14 IC50/(nM) | Anti-proliferative activity v. U937 cells Example 16 IC50/(μM) |
|---|---|---|---|---|---|---|
| TGX-286 | 5000 | 2 | 100 | 500 | 5 | 5 |
| KN-327 | | | 200 | 250 | 78 | 20 |

FORMULATION EXAMPLES

Example 1

Making and Administering Pharmaceutical Compositions that Contain Pyridine-Substituted Compounds Some of the preferred pharmaceutical formulations of the present invention are described below.

Tablet Formulation for Oral Administration:

The ingredients of a tablet formulation for oral administration are listed in Table IV below. Tablets A, B, and C are prepared by wet granulation, with the povidone, of the first six ingredients listed in Table IV, followed by the addition of the magnesium stearate and subsequent compression.

TABLE IV

| | Milligrams per Tablet | | |
|---|---|---|---|
| | Tablet A | Tablet B | Tablet C |
| Active ingredient | 25 | 25 | 25 |
| Avicel | 13 | — | 7 |
| Lactose | 78 | 47 | — |
| Starch (maize) | — | 9 | — |
| Starch (pregelatinised, NF15) | — | — | 32 |
| Sodium starch glycollate | 5 | — | — |
| Povidone | 3 | 3 | — |
| Magnesium stearate | 1 | 1 | 1 |
| Total | 125 | 85 | 85 |

Tablet Formulation for Sublingual Administration:

The ingredients of two tablet formulations for sublingual administration are listed in Table V below. Tablets A and B are prepared by wet granulation, with the povidone, of the first six ingredients listed in Table V, followed by the addition of the magnesium stearate and subsequent compression.

TABLE V

| | Milligrams per Tablet | |
|---|---|---|
| | Tablet A | Tablet B |
| Active ingredient | 25 | 25 |
| Avicel | 10 | — |
| Lactose | — | 36 |
| Mannitol | 51 | 57 |
| Sucrose | — | 3 |
| Acacia | — | 3 |
| Povidone | 3 | — |
| Magnesium stearate | 1 | 1 |
| Total | 90 | 125 |

Tablet Formulation for Buccal Administration:

A tablet for buccal administration is prepared by admixing the ingredients listed in Table VI below, followed by direct compression of the admixed ingredients.

TABLE VI

| | Milligrams per Tablet |
|---|---|
| Active ingredient | 25 |
| Hydroxypropylmethyl cellulose (HPMC) | 25 |
| Polycarbophil | 39 |
| Magnesium stearate | 1 |
| Total | 90 |

Powder-Filled Capsule Formulation:

The ingredients of two powder-filled capsule formulations are listed in Table VII below. Capsules A and B are prepared by admixing the ingredients, and filing two-part hard gelatin capsules with the resulting mixture.

TABLE VII

| | Milligrams per Tablet | |
|---|---|---|
| | Capsule A | Capsule B |
| Active ingredient | 25 | — |
| Avicel | 45 | — |
| Lactose | 153 | — |
| Starch (1500 NF) | — | 117 |
| Sodium starch glycollate | — | 6 |
| Magnesium stearate | 2 | 2 |
| Total | 225 | 150 |

Liquid-Filled Capsule Formulation:

The ingredients of two liquid-filled capsule formulations are listed in Table VIII below. Capsule A is prepared by melting the Macrogol 4000 BP, dispersing the active ingredient in the melt, and filling two-part hard gelatin capsules therewith. Capsule B may be prepared by dispersing the active ingredient in the lecithin and arachis oil, and filling soft, elastic gelatin capsules with the resulting dispersion.

TABLE VIII

| | Milligrams per Tablet | |
|---|---|---|
| | Capsule A | Capsule B |
| Active ingredient | 25 | 25 |
| Macrogol 4000 USP | 200 | — |
| Lecithin | — | 100 |
| Arachis oil | — | 100 |
| Total | 225 | 225 |

Controlled-Release Capsule Formulation:

A capsule formulation for controlled release is prepared by mixing and extruding the first four ingredients listed in Table IX below, and spheronizing and drying the extrudate. The dried pellets are coated with the ethyl cellulose as a release-controlling membrane, and the resulting pellets are filled into two-part hard gelatin capsules.

TABLE IX

| | Milligrams per Capsule |
|---|---|
| Active ingredient | 25 |
| Avicel | 123 |
| Lactose | 62 |
| Triethyl citrate | 3 |
| Ethyl cellulose | 12 |
| Total | 225 |

Intravenous Formulation:

The intravenous formulation containing the ingredients listed in Table X below is prepared by taking up the active ingredient in the citrate buffer, and the pH of the solution is then adjusted to pH 7 with hydrochloric acid. The resulting solution is made up to volume, and is subsequently filtered through a micropore filter into sterile glass vials which are sealed and oversealed after filling.

TABLE X

| | % by weight |
|---|---|
| Active ingredient | 2 |
| Hydrochloric acid (citrate buffer) | q.s. to pH 7 |
| Water for injections | to 100% |

Intranasal Formulation:

An intranasal formulation containing the ingredients listed in Table XI below is prepared by taking up the active ingredient in a mixture of the hydroxybenzoates, and the pH of the solution is then adjusted to pH 7 with hydrochloric acid in citrate buffer. The resulting solution is made up to volume, and is subsequently filtered through a micropore filter into sterile glass vials which are sealed and oversealed after filling.

TABLE XI

| | % by weight |
|---|---|
| Active ingredient | 0.5 |
| Hydrochloric acid in citrate buffer | q.s. to pH 7 |
| Methyl hydroxybenzoate | 0.2 |
| Propyl hydroxybenzoate | 0.2 |
| Water for injections | to 100% |

Intramuscular-Injection Formulation:

A formulation for intramuscular injection containing the ingredients listed in Table XII below is prepared by dissolving the active ingredient in the glycofurol. The benzyl alcohol is then added and dissolved, and water is added to bring the final volume to 3 ml. The mixture is then filtered through a micropore filter into sterile glass vials which are sealed and oversealed after filling.

TABLE XII

| | |
|---|---|
| Active ingredient | 0.05 g |
| Benzyl alcohol | 0.1 g |
| Glycofuro 751 | 1.45 g |
| Water for injections | q.s. to 3.00 ml |

Syrup Formulation:

A syrup formulation containing the ingredients listed in Table XIII below is prepared by dissolving the sodium benzoate in a portion of purified water, and the sorbitol solution is then added. Subsequently, the active ingredient is added and dissolved. The resulting solution is then mixed with the glycerol and made up to the required volume with purified water.

TABLE XIII

| | |
|---|---|
| Active Ingredient | 0.05 g |
| Sorbitol solution | 1.5 g |
| Glycerol | 1.0 g |
| Sodium benzoate | 0.005 g |
| Flavor | 0.0125 ml |

Suppository Formulation:

A suppository formulation containing the ingredients listed in Table XIV below is prepared by melting one-fifth of the Witepsol in a steam-jacketed pan at a maximum temperature of 45° C. The active ingredient is then sifted through a 200 μm sieve and mixed with the molten base using a Silverson mixer fitted with a cutting head until a smooth dispersion is achieved. Maintaining the mixture at 45° C., the remaining Witepsol H15 is added to the suspension which is stirred to ensure a homogenous mix. The entire suspension is then passed through a 250 μm stainless steel screen and, with continuous stirring, allowed to cool to 40° C. At a temperature of between 38 and 40° C., 2.0 g aliquots of the mixture are filled into suitable plastic molds. The resulting suppositories are allowed to cool to room temperature.

TABLE XIV

|  | Milligrams per Suppository |
| --- | --- |
| Active ingredient (63 μm)[1] | 50 |
| Hard fat, USP (Witepsol H15 - dynamit NoBel) | 1950 |
| Total | 2000 |

[1]The active ingredient is used as a powder wherein at least 90% of the particles are of 63 μm diameter or less.

Aerosol Formulation:

An aerosol formulation containing the ingredients listed in Table XV below is prepared by mixing the active compound with ethanol, and water is added for injection. The solution is subsequently added to a portion of the Propellant 22, cooled to −30° C., and transferred to a filling device. The required amount is then fed to a stainless steel container and diluted with the remainder of the propellant. The valve units are then fitted to the container.

TABLE XV

|  | % by weight |
| --- | --- |
| Active ingredient | 0.25 |
| Ethanol | 10 |

TABLE XV-continued

|  | % by weight |
| --- | --- |
| Water for injections | 19.75 |
| Propellant 22 (chlorodifluoromethane) | 70 |
| Total | 100 |

Pessary Formulation:

A pessary formulation is prepared by directly mixing the ingredients listed in the Table XVI below. Pessaries are prepared by compressing the resulting mixture.

TABLE XVI

|  | Milligrams per Pessary |
| --- | --- |
| Active ingredient (63 μm)[1] | 50 |
| Anhydrous dextrose | 470 |
| Potato starch | 473 |
| Magnesium stearate | 473 |
| Water for injections | 1000 |

The active ingredient is used as a powder wherein at least 90% of the particles are of 63 μm diameter or less.

The invention claimed is:

1. A compound which is (±)-7-methyl-2-morpholin-4-yl-9-(1-phenylaminoethyl)-pyrido[1,2-a]pyrimidin-4-one, (±)-2-({1-[7 methyl 2 (morpholin-4-yl)-4-oxo pyrido[1,2-a]pyrimidin 9-yl]ethyl}amino)benzoic acid, (±)-2-({1-[7-methyl-2-(morpholin-4-yl)-4-oxo-pyrido[1,2-a]pyrimidin-9-yl]ethyl}amino)benzonitrile, (±) methyl 2-({1-[7-methyl-2-(morpholin-4-yl)-4-oxo-pyrido[1,2-a]pyrimidin-9-yl]ethyl}amino)benzoate, or (±)-7-methyl-2-(morpholin-4-yl)-9-(1-{[2-(2H-tetrazol-5-yl)phenyl]amino}ethyl)-pyrido[1,2-a]pyrimid-4-one.

* * * * *

UNITED STATES PATENT AND TRADEMARK OFFICE
CERTIFICATE OF CORRECTION

PATENT NO. : 7,598,377 B2  Page 1 of 1
APPLICATION NO. : 10/522777
DATED : October 6, 2009
INVENTOR(S) : Jackson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 658 days.

Signed and Sealed this

Twenty-eighth Day of September, 2010

David J. Kappos
*Director of the United States Patent and Trademark Office*